US009260491B2

(12) United States Patent
Takaiwa et al.

(10) Patent No.: US 9,260,491 B2

(45) Date of Patent: Feb. 16, 2016

(54) PROTEIN HAVING IMMUNOGENICITY OF CEDAR POLLEN, POLYNUCLEOTIDE ENCODING THE PROTEIN, AND USE THEREOF

(75) Inventors: Fumio Takaiwa, Ibaraki (JP); Hidenori Takagi, Ibaraki (JP); Yuhya Wakasa, Ibaraki (JP); Yuji Fujii, Tokyo (JP); Tomotaka Shinya, Tokyo (JP); Saori Kasahara, Tokyo (JP)

(73) Assignees: NIPPON PAPER INDUSTRIES CO., LTD., Tokyo (JP); NATIONAL INSTITUTE OF AGROBIOLOGICAL SCIENCES, Tsukuba-shi (JP)

( * ) Notice: Subject to any disclaimer, the term of this patent is extended or adjusted under 35 U.S.C. 154(b) by 849 days.

(21) Appl. No.: 13/504,636

(22) PCT Filed: Oct. 28, 2010

(86) PCT No.: PCT/JP2010/069218

§ 371 (c)(1), (2), (4) Date: Apr. 27, 2012

(87) PCT Pub. No.: WO2011/052697

PCT Pub. Date: May 5, 2011

(65) Prior Publication Data

US 2012/0244176 A1 Sep. 27, 2012

(30) Foreign Application Priority Data

Oct. 30, 2009 (JP) ................................ 2009-249919

(51) Int. Cl.

*A61K 39/36* (2006.01)
*C07K 14/415* (2006.01)
*A61K 38/00* (2006.01)

(52) U.S. Cl.

CPC ............... *C07K 14/415* (2013.01); *A61K 39/36* (2013.01); *A61K 38/00* (2013.01)

(58) Field of Classification Search

None

See application file for complete search history.

(56) References Cited

U.S. PATENT DOCUMENTS

| | | | | |
|---|---|---|---|---|
| 6,982,326 B1 | 1/2006 | Griffith et al. | | |
| 2007/0136896 A1* | 6/2007 | Takaiwa et al. | ............... | 800/288 |

FOREIGN PATENT DOCUMENTS

| | | |
|---|---|---|
| JP | 8-505284 | 6/1996 |
| JP | 10-259198 | 9/1998 |
| JP | 2000-327699 | 11/2000 |
| JP | 2004 321079 | 11/2004 |
| WO | WO 93/01213 A1 | 1/1993 |
| WO | WO 94/11512 A2 | 5/1994 |

OTHER PUBLICATIONS

GenBank BAA05543.1 (Feb. 2008; appended to the Office Action).*

Hiroshi Yasueda, et al., "Isolation and partial characterization of the major allergen from Japanese cedar (*Cryptomeria japonica*) pollen" Journal of Allergy and Clinical Immunology, vol. 71, No. 1, Part 1, Jan. 1983, pp. 77-86.

Madoka Taniai, et al., "N-terminal amino acid sequence of a major allergen of Japanese cedar pollen (Cry j I)", Federation of European Biochemical Societies, vol. 239, No. 2, Nov. 1988, pp. 329-332.

M. Sakaguchi, et al., "Identification of the second major allergen of Japanese cedar pollen", Allergy, vol. 45, No. 4, 1990, pp. 309-312.

Chu Chih-Ching, "The $N_6$ Medium and its applications to anther culture of cereal crops", In: Proceedings of Symposium on Plant Tissue Culture, Science Press. Peking, 1978, pp. 43-50.

Office Action issued Sep. 24, 2014, in Japanese Patent Application No. 2011-538487 with English translation.

Combined Chinese Office Action and Search Report issued Mar. 15, 2013, in Chinese Patent Application No. 201080049711.8 with English translation of category of cited documents.

Futamura N., et al., "Allergen Cry j 2 [*Cryptomeria japonica*]", GenBank: BAC23083.1, Oct. 2, 2007, 1 page.

Sone T., et al., "Cry j IB precursor [*Cryptomeria japonica*]", GenBank: BAA05543.1, Feb. 16, 2008, 1 page.

Takagi, H., et al., "A rice-based edible vaccine expressing multiple T cell epitopes induces oral tolerance for inhibition of Th2-mediated IgE responses," Proceedings of the National Academy of Science, vol. 102, No. 48, pp. 17525-17530, (Nov. 29, 2005).

Yang, L., et al., "Development of transgenic rice seed accumulating a major Japanese cedar pollen allergen (Cry j 1) structurally disrupted for oral immunotherapy," Plant Biotechnology Journal, vol. 5, No. 6, pp. 815-826 (2007).

Yokoyama, S., et al., "Prevention of pollen allergy against Japanese cedar by rice based edible vaccine expressing multiple T cell epitopes," Allergy in Practice, vol. 27, No. 1, (pp. 17-23), (2007) (with English abstract).

Takaiwa, F., et al., "Development of rice seed-based edible vaccine for Japanese cedar pollinosis," JJIAO, vol. 26, No. 3, pp. 233-237, (2008) (with English abstract).

International Search Report Issued Dec. 7, 2010 in PCT/JP10/69218 Filed Oct. 28, 2010.

* cited by examiner

*Primary Examiner* — Elizabeth McElwain

*Assistant Examiner* — Stephen Uyeno

(74) *Attorney, Agent, or Firm* — Oblon, McClelland, Maier & Neustadt, L.L.P.

(57) ABSTRACT

It is an object of the present invention to provide a protein that can successfully treats almost all patients with cedar pollinosis and can be ingested as a food. That is, the present invention provides a protein comprising an amino acid sequence represented by SEQ ID NO:1 or comprising an amino acid sequence having a mutation(s) in said amino acid sequence, and having an immunogenicity of a cedar pollen; a polynucleotide encoding said protein; a vector comprising said polynucleotide; a transformant comprising said polynucleotide or said vector; and intended uses of said protein, said polynucleotide, and said transformant.

13 Claims, 5 Drawing Sheets

PROTEIN HAVING IMMUNOGENICITY OF CEDAR POLLEN, POLYNUCLEOTIDE ENCODING THE PROTEIN, AND USE THEREOF

TECHNICAL FIELD

The present invention relates to a novel protein having an immunogenicity of a cedar pollen, and a polynucleotide encoding the protein.

BACKGROUND ART

Pollinosis refers to an allergic symptom caused by a pollen that has entered the body, and the number of patients with the pollinosis continues to increase. The pollen that is a cause of the pollinosis is typified by a cedar pollen. Two kinds of proteins, i.e., Cryj1 (see Patent Document 1 and Nonpatent Literature 1) and Cryj2 (see Patent Document 2, and Nonpatent Literatures 2 and 3) have been known to be as allergens of the cedar pollen. It has been known that most patients with cedar pollinosis cause an allergic response to both Cryj1 and Cryj2, or to either Cryj1 or Cryj2.

A peptide immunotherapy in which a peptide composed of a T cell epitope in the allergen is administered to the patient is available as one of therapies for the pollinosis. The peptide immunotherapy has merits that no risky side effect such as anaphylaxis is caused and that the symptom is alleviated in a shorter period of time compared with a hyposensitization therapy in which the allergen itself is administered to the patient.

Patent Documents 3 and 4 describe that a peptide containing multiple different human T cell epitopes derived from the allergen of the cedar pollen can be used for the immunotherapy. Patent Document 4 describes that about 57% of the patients with cedar pollinosis can be treated successfully with the above peptide.

RELATED ART DOCUMENTS

Patent Literature

Patent Document 1: International Publication No. WO93/01213

Patent Document 2: JP Hei-8-505284

Patent Document 3: JP Hei-10-259198-A

Patent Document 4: JP 2000-327699-A

Nonpatent Literature

Nonpatent Literature 1: Yasuda, H. et al., Allergy Clin. Immunol., 71, 77-86, 1983

Nonpatent Literature 2: Taniai, M. et al., FEBS Letters, 239, 329-332, 1988

Nonpatent Literature 3: Sakaguchi, H. et al., Allergy, 45, 309-312, 1990.

DISCLOSURE OF THE INVENTION

Technical Problem

However, the peptides described in Patent Documents 3 and 4 were not sufficient in effect of treating the pollinosis in that all of the patients with cedar pollinosis were not treated successfully with such peptides.

It is an object of the present invention to provide a protein that successfully treats almost all of the patients with cedar pollinosis and can be ingested as a food.

Solution to Problem

As a result of extensive studies for solving the above problem, the present inventors focused on amino acid sequences of Cryj1 and Cryj2, which are allergens of the cedar pollen, and tried to modify these sequences. As a result, the present inventors have found that a protein comprising an amino acid sequence obtained by giving a certain modification to the original amino acid sequence has a reduced binding property to IgE and high safety because the protein has a three dimensional structure different from that of a cedar pollen antigen with keeping an immunogenicity of a cedar pollen. Further, the present inventors analyzed genetic information encoding the above protein and have found that a mass production of the protein and a plant comprising the protein is feasible. The present invention is based on such findings.

[1] A protein selected from the group consisting of following (A) to (C):(A) a protein comprising an amino acid sequence represented by SEQ ID NO:1;

(B) a protein comprising an amino acid sequence having one or several amino acid substitution(s), deletion(s), insertion(s), and/or addition(s) in the amino acid sequence represented by SEQ ID NO:1, and having an immunogenicity of a cedar pollen; and (C) a protein comprising an amino acid sequence having 90% or more identity to the amino acid sequence represented by SEQ ID NO:1, and having the immunogenicity of the cedar pollen.

[2] A polynucleotide selected from the group consisting of following (a) to (c):

(a) a polynucleotide encoding an amino acid sequence represented by SEQ ID NO:1;

(b) a polynucleotide encoding a protein comprising an amino acid sequence having one or several amino acid substitution(s), deletion(s), insertion(s), and/or addition(s) in the amino acid sequence represented by SEQ ID NO:1, and having an immunogenicity of a cedar pollen; and (c) a polynucleotide encoding a protein comprising an amino acid sequence having 90% or more identity to the amino acid sequence represented by SEQ ID NO:1, and having the immunogenicity of the cedar pollen.

[3] A protein selected from the group consisting of following (D) to (F):

(D) a protein comprising an amino acid sequence represented by SEQ ID NOS:2 to 4;

(E) a protein comprising an amino acid sequence having one or several amino acid substitution(s), deletion(s), insertion(s), and/or addition(s) in the amino acid sequence represented by any one of SEQ ID NOS:2 to 4, and having an immunogenicity of a cedar pollen; and (F) a protein comprising an amino acid sequence having 90% or more identity to the amino acid sequence represented any one of SEQ ID NOS:2 to 4, and having the immunogenicity of the cedar pollen.

[4] A polynucleotide selected from the group consisting of following (d) to (f):

(d) a polynucleotide encoding an amino acid sequence represented by any one of SEQ ID NOS:2 to 4;

(e) a polynucleotide encoding a protein comprising an amino acid sequence having one or several amino acid substitution(s), deletion(s), insertion(s), and/or addition(s) in the amino acid sequence represented by any one of SEQ ID NOS:2 to 4, and having an immunogenicity of a cedar pollen; and (f) a polynucleotide encoding a protein comprising an amino acid sequence having 90% or more identity to the amino acid sequence represented any one of SEQ ID NOS:2 to 4, and having the immunogenicity of the cedar pollen.

[5] The polynucleotide according to above [4], selected from the group consisting of following (p) to (r):

(p) a polynucleotide comprising a nucleotide sequence represented by SEQ ID NO:5;

(q) a polynucleotide comprising a nucleotide sequence represented by any one of SEQ ID NOS:6 to 8; and (r) a polynucleotide comprising the nucleotide sequence represented by SEQ ID NO:5 and the nucleotide sequence represented by any one of SEQ ID NOS:6 to 8.

[6] A vector comprising the polynucleotide according to any one of above [2], [4] and [5].

[7] A transformant in which the polynucleotide according to any one of above [2], [4] and [5] or the vector according to above [6] has been introduced.

[8] The transformant according to above [7], wherein said transformant is a plant.

[9] The transformant according to above [7], wherein said transformant is a gramineous plant.

[10] A method for producing the protein according to above [1] or [3], comprising expressing said polynucleotide in the transformant according to any one of above [7] to [9] and collecting the produced protein.

[11] A method for imparting an immunogenicity of a cedar pollen to a plant by introducing the polynucleotide according to any one of above [2], [4] and [5] into the plant.

[12] A method for producing a plant body having an immunogenicity of a cedar pollen, comprising producing a vector comprising the polynucleotide according to above [2] and/or above [4], introducing said vector into a plant organ, a plant tissue, or a plant cell to obtain a transformant, and growing the plant body from said transformant.

[13] A therapeutic agent or a prophylactic agent for a cedar pollinosis, containing one or two or more selected from the protein according to above [1] or [3] and the transformant according to any one of above [7] to [9] as an active ingredient.

[14] A method for treating or preventing a cedar pollinosis, containing administration of one or two or more selected from the protein according to above [1] or [3] and the transformant according to any one of above [7] to [9] to a human.

Effect of the Invention

The protein provided by the present invention and having the immunogenicity of the cedar pollen has less potential to not cause anaphylaxic reaction in the body because the binding property of the protein to a pollen-specific IgE antibody is low although the protein exerts the immunogenicity of the cedar pollen in almost all of the patients with cedar pollinosis. The protein of the present invention can be said to be useful as a therapeutic agent or a prophylactic agent for the cedar pollinosis that covers the patients with the cedar pollinosis because almost all of the patient with the cedar pollinosis respond to the immunogenicity of the cedar pollen allergens, Cryj1 and Cryj2. Thus, the protein having the immunogenicity of the cedar pollen is useful for the treatment of the cedar pollinosis, by itself or as the plant comprising the protein.

The genetic information of the protein having the immunogenicity of the cedar pollen is provided by the present invention. Thus, based on this, it is also possible to produce the protein having the immunogenicity of the cedar pollen, a transformant containing the protein, and progenies (rice plant, and the like) of the transformant on a large scale.

EMBODIMENTS FOR CARRYING OUT THE INVENTION

Figure 1:
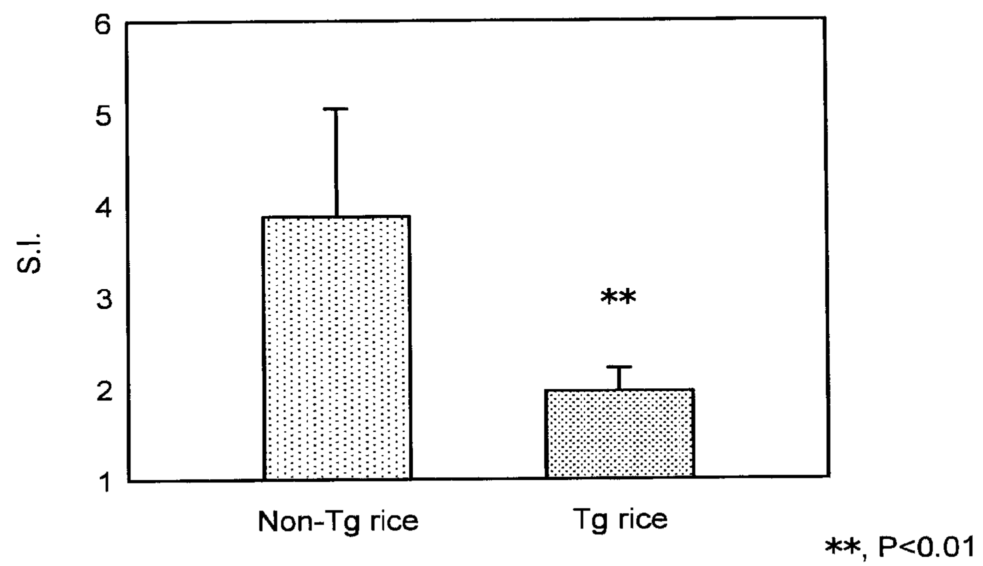
FIG. 1 is a graph showing proliferative activity of T cells in an experimental group of orally administering Tg rice seeds and an experimental group of orally administering Non-Tg rice seeds.
Figure 2:
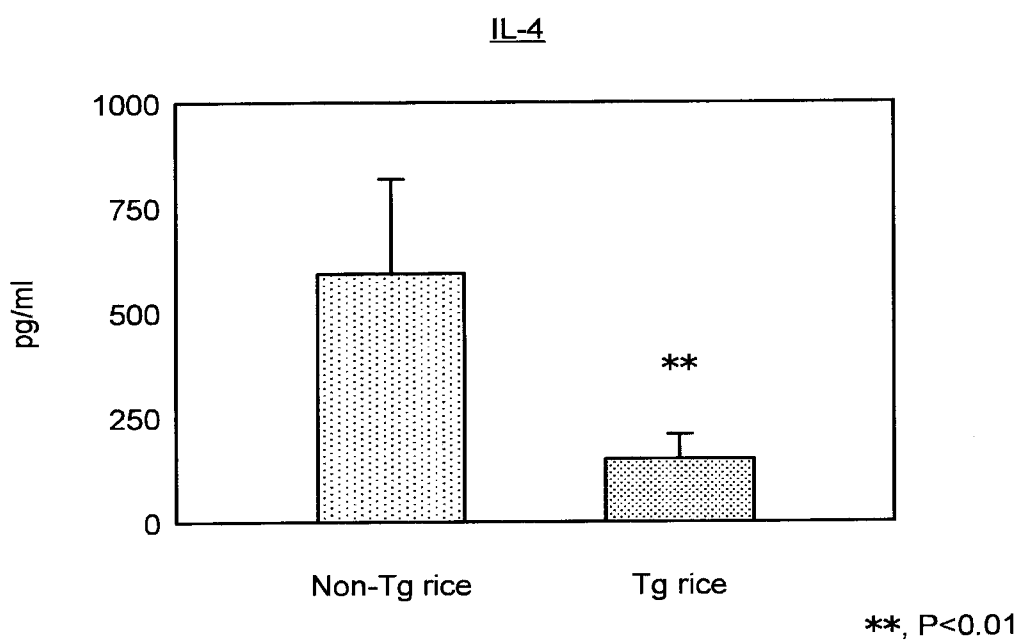
FIG. 2 is a graph showing amounts of IL-4 produced in the experimental group of orally administering the Tg rice seeds and the experimental group of orally administering the Non-Tg rice seeds.
Figure 3:
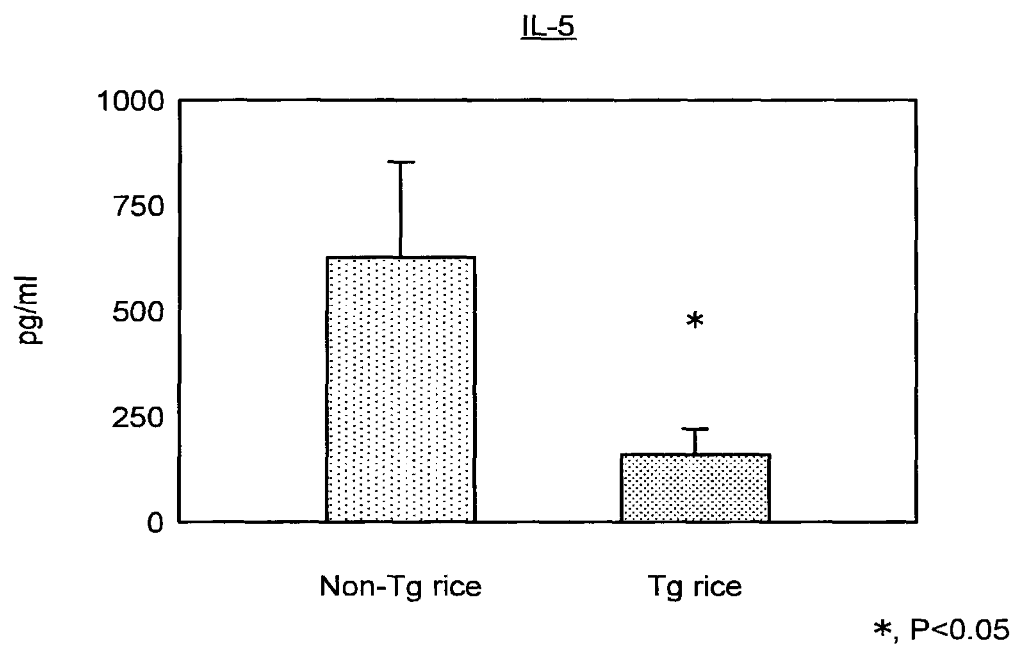
FIG. 3 is a graph showing amounts of IL-5 produced in the experimental group of orally administering the Tg rice seeds and the experimental group of orally administering the Non-Tg rice seeds.
Figure 4:
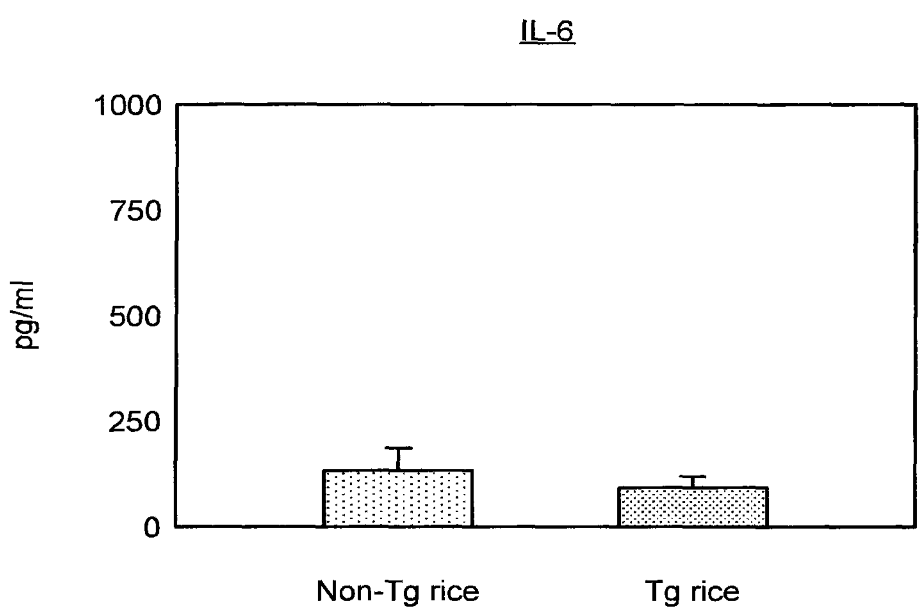
FIG. 4 is a graph showing amounts of IL-6 produced in the experimental group of orally administering the Tg rice seeds and the experimental group of orally administering the Non-Tg rice seeds.
Figure 5:
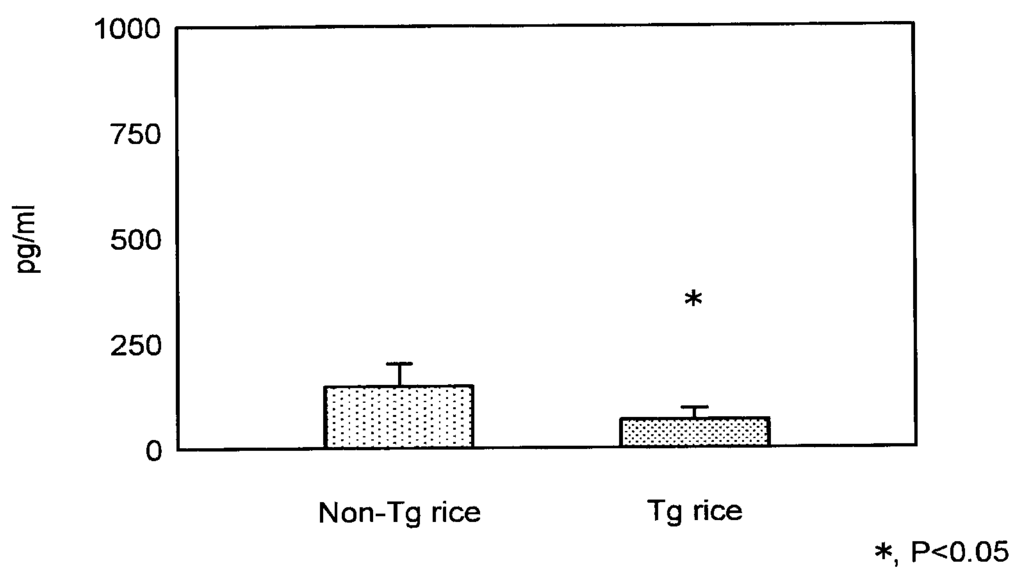
FIG. 5 is a graph showing amounts of IL-10 produced in the experimental group of orally administering the Tg rice seeds and the experimental group of orally administering the Non-Tg rice seeds.
Figure 6:
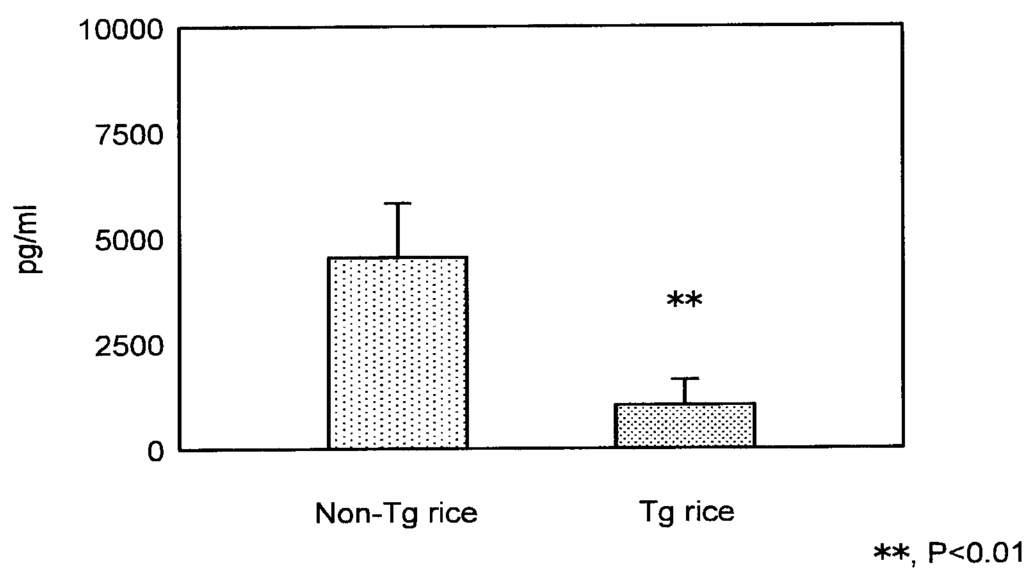
FIG. 6 is a graph showing amounts of IL-13 produced in the experimental group of orally administering the Tg rice seeds and the experimental group of orally administering the Non-Tg rice seeds.
Figure 7:
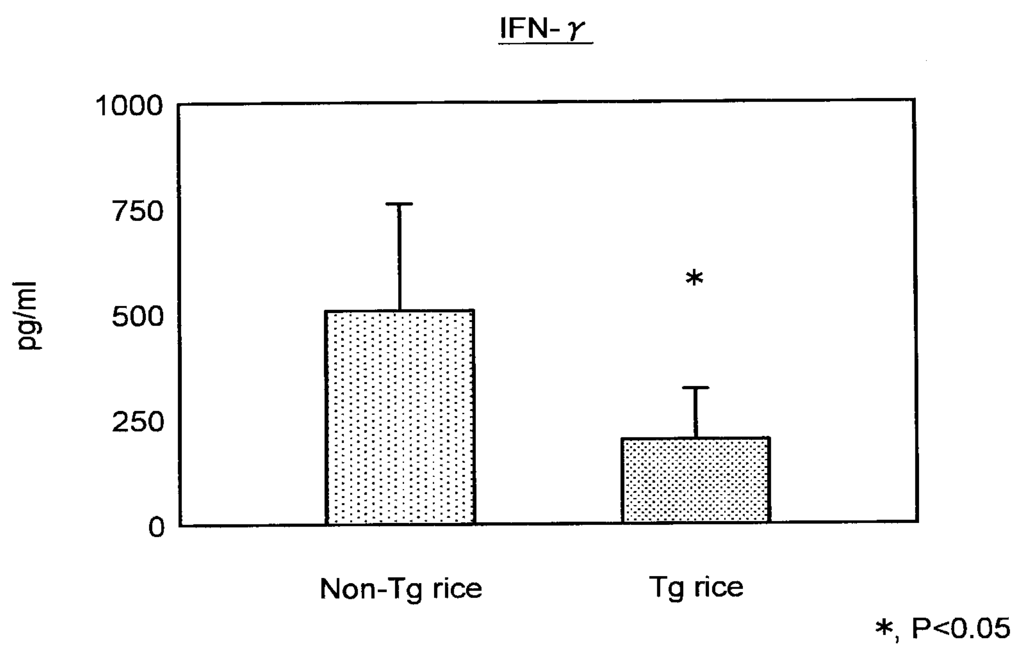
FIG. 7 is a graph showing amounts of IFN-γ produced in the experimental group of orally administering the Tg rice seeds and the experimental group of orally administering the Non-Tg rice seeds.

The protein of the present invention is a protein having the immunogenicity of a cedar (Sugi/*Cryptomeria*) pollen. The immunogenicity of the cedar pollen means being recognized as an antigen by a cedar pollen-specific T cell, and is a nature that a cedar pollen allergen comprises. The cedar pollen allergen may include Cryj1 and Cryj2. The protein of the present invention has such an immunogenicity of the cedar pollen, and its activity is preferably equivalent to the immunogenicity of either Cryj1 or Cryj2 or both Cryj1 and Cryj2.

Examples of the protein having the immunogenicity of the cedar pollen may include a protein (A) comprising an amino acid sequence represented by SEQ ID NO:1. The amino acid sequence represented by SEQ ID NO:1 was designed by shuffling an amino acid sequence of the cedar pollen allergen Cryj2. That is, this sequence was obtained by linking a portion of the 93rd to 388th amino acids, a portion of the 59th to 92nd amino acids and a portion of the 1st to 58th amino acids counted from an N terminus of the amino acid sequence of Cryj2 in this order. The protein (A) has the immunogenicity of the cedar pollen, and preferably the immunogenicity equivalent to that of Cryj2.

Examples of the protein having the immunogenicity of the cedar pollen may also include a protein (D) comprising one or two or more selected from amino acid sequences represented by SEQ ID NOS: 2 to 4. Each amino acid sequence represented by SEQ ID NOS: 2 to 4 was designed by fragmenting Cryj1 into three fragmentations. That is, the amino acid sequence represented by SEQ ID NO:2 corresponds to a portion of the 1st to 144th amino acids counted from the N terminus of the amino acid sequence of Cryj1. The amino acid sequence represented by SEQ ID NO:3 corresponds to a portion of the 126th to 257th amino acids counted from the N terminus of the amino acid sequence of Cryj1. The amino acid sequence represented by SEQ ID NO:4 corresponds to a portion of the 231st to 353rd amino acids counted from the N terminus of the amino acid sequence of Cryj1. The protein (D) has the immunogenicity of the cedar pollen, and preferably the immunogenicity equivalent to that of Cryj1.

The protein (D) may have any one of the amino acid sequence represented by SEQ ID NO:2, the amino acid sequence represented by SEQ ID NO:3, and the amino acid sequence represented by SEQ ID NO:4. The protein (D) may have two or more thereof in combination, and preferably has all of them. When the protein has two or more of the amino acid sequences, an order of linking is not particularly limited. However, when the protein has all of the three sequences, it is preferable to link the amino acid sequence represented by SEQ ID NO:3, the amino acid sequence represented by SEQ ID NO:2, and the amino acid sequence represented by SEQ ID NO:4 in this order.

Examples of the protein having the immunogenicity of the cedar pollen may further include a protein (G) comprising the amino acid sequence represented by SEQ ID NO:1 and the amino acid sequence represented by any of SEQ ID NOS:2 to 4. The protein (G) has the immunogenicity of the cedar pollen and preferably the immunogenicity equivalent to that of Cryj1 and Cryj2. The protein (G) may comprise one or two or more amino acid sequences selected from the amino acid sequence represented by SEQ ID NO:2, the amino acid sequence represented by SEQ ID NO:3, and the amino acid sequence represented by SEQ ID NO:4 in addition to the amino acid sequence represented by SEQ ID NO:1, and preferably comprises all of the amino acid sequences represented by SEQ ID NOS:2 to 4.

The order of linking the amino acid sequence represented by SEQ ID NO:1 and the amino acid sequence represented by any of SEQ ID NOS:2 to 4 in the protein (G) is not limited, and it is preferable to link in the order of the amino acid sequence represented by any of SEQ ID NOS:2 to 4 and the amino acid sequence represented by SEQ ID NO:1 from an N terminal side. When the protein (G) comprises all of the amino acid sequences represented by SEQ ID NOS:2 to 4, the order of linking these amino acid sequences is not particularly limited, but it is preferable to link the amino acid sequence represented by SEQ ID NO:3, the amino acid sequence represented by SEQ ID NO:2, and the amino acid sequence represented by SEQ ID NO:4 in this order.

Both of an origin of the protein having the immunogenicity of the cedar pollen and a method for obtaining the protein are not particularly limited. That is, examples of the protein having the immunogenicity of the cedar pollen may include native proteins, proteins expressed by recombinant polynucleotides by gene engineering techniques, and proteins obtained by chemical synthesis. And, for example, the protein (A) may be obtained by shuffling the cedar pollen allergen Cryj2. Also for example, the protein (D) may be obtained by fragmenting the cedar pollen allergen Cryj1 into three fragments [F1 (fragment 1: 1 aa to 144 aa), F2 (fragment 2: 126 aa to 257 aa), and F3 (fragment 3: 231 aa to 353 aa)]. Further, for example, a protein (I) may be obtained by linking the protein obtained by shuffling the cedar pollen allergen Cryj2 to the protein obtained by fragmenting the cedar pollen allergen Cryj1 into three fragments.

The protein having the immunogenicity of the cedar pollen may be not only those having the amino acid sequence itself represented by SEQ ID NO:1 and the amino acid sequence itself represented by any of SEQ ID NOS:2 to 4 such as the protein (A), the protein (D), and the protein (G) described above but also proteins homologous thereto, i.e., proteins comprising an amino acid sequence having a modification(s) in the each amino acid sequence, as long as the protein has the immunogenicity of the cedar pollen.

Examples of the protein comprising the amino acid sequence having the modification(s) in the amino acid sequence of the protein (A) may include the following proteins (B) and (C):

(B) The protein comprising an amino acid sequence having one or several amino acid substitutions, deletions, insertions, and/or additions in the amino acid sequence represented by SEQ ID NO:1, and having the immunogenicity of the cedar pollen; and (C) The protein comprising an amino acid sequence having 90% or more identity to the amino acid sequence represented by SEQ ID NO:1, and having the immunogenicity of the cedar pollen.

Examples of the proteins comprising the amino acid sequence having the modification(s) in the amino acid sequence of the protein (D) may include proteins (E) and (F):

(E) The protein comprising an amino acid sequence having one or several amino acid substitutions, deletions, insertions, and/or additions in the amino acid sequence represented by any one of SEQ ID NOS:2 to 4, and having the immunogenicity of the cedar pollen; and (F) The protein comprising an amino acid sequence having 90% or more identity to the amino acid sequence represented by any one of SEQ ID NOS:2 to 4, and having the immunogenicity of the cedar pollen.

The protein (E) may comprise the amino acid sequence having the substitution, the deletion, the insertion, and/or the addition in any of or two or more of the amino acid sequence represented by SEQ ID NO:2, the amino acid sequence represented by SEQ ID NO:3, and the amino acid sequence represented by SEQ ID NO:4, and may have the amino acid sequence represented by any of SEQ ID NOS:2 to 4 not subjected to modification such as the substitution, in addition thereto. The protein (F) may comprise the amino acid sequence having 90% or more identity to any of or two or more of the amino acid sequence represented by SEQ ID NO:2, the amino acid sequence represented by SEQ ID NO:3, and the amino acid sequence represented by SEQ ID NO:4. The protein (F) may have the amino acid sequence represented by any of SEQ ID NOS:2 to 4 not subjected to the substitution or the like, in addition thereto.

Examples of the protein comprising the amino acid sequence having the modification(s) in the amino acid sequence of the protein (G) may include proteins (H) to (O).

(H) The protein comprising the amino acid sequence represented by SEQ ID NO:1 and an amino acid sequence having one or several amino acid substitutions, deletions, insertions, and/or additions in one or two or more amino acid sequences in the amino acid sequences represented by SEQ ID NOS:2 to 4, and having the immunogenicity of the cedar pollen.

(I) The protein comprising the amino acid sequence represented by SEQ ID NO:1 and an amino acid sequence having 90% or more identity to one or two or more amino acid sequences in the amino acid sequences represented by SEQ ID NOS:2 to 4, and having the immunogenicity of the cedar pollen.

(J) The protein comprising an amino acid sequence having one or several amino acid substitutions, deletions, insertions, and/or additions in the amino acid sequence represented by SEQ ID NO:1 and one or two or more amino acid sequences in the amino acid sequences represented by SEQ ID NOS:2 to 4, and having the immunogenicity of the cedar pollen.

(K) The protein comprising an amino acid sequence having 90% or more identity to the amino acid sequence represented by SEQ ID NO:1 and one or two or more amino acid sequences in the amino acid sequences represented by SEQ ID NOS:2 to 4, and having the immunogenicity of the cedar pollen.

(L) The protein comprising the amino acid sequence having one or several amino acid substitutions, deletions, insertions, and/or additions in the amino acid sequence represented by SEQ ID NO:1 and the amino acid sequence having one or several amino acid substitutions, deletions, insertions, and/or additions in one or two or more amino acid sequences in the amino acid sequences represented by SEQ ID NOS:2 to 4, and having the immunogenicity of the cedar pollen.

(M) The protein comprising the amino acid sequence having 90% or more identity to the amino acid sequence represented by SEQ ID NO:1 and the amino acid sequence having 90% or more identity to one or two or more amino acid sequences in the amino acid sequences represented by SEQ ID NOS:2 to 4, and having the immunogenicity of the cedar pollen.

(N) The protein comprising the amino acid sequence having 90% or more identity to the amino acid sequence represented by SEQ ID NO:1 and the amino acid sequence having one or several amino acid substitutions, deletions, insertions, and/or additions in one or two or more amino acid sequences in the amino acid sequences represented by SEQ ID NOS:2 to 4, and having the immunogenicity of the cedar pollen.

(O) The protein comprising the amino acid sequence having one or several amino acid substitutions, deletions, insertions, and/or additions in the amino acid sequence represented by SEQ ID NO:1 and the amino acid sequence having 90% or more identity to one or two or more amino acid sequences in the amino acid sequences represented by SEQ ID NOS:2 to 4, and having the immunogenicity of the cedar pollen.

The number of the substituted, deleted, inserted, and/or added amino acid residues in above each protein is one or several as described above. The number is typically 1 to 15, for example, 1 to 10, preferably 1 to 7, more preferably 1 to 5, and still more preferably 1 to 3. A technique of introducing one or several mutation into an amino acid sequence to make a protein having the same nature as an original amino acid sequence is generally well-known to those skilled in the art. When an amino acid is substituted with an amino acid having the same nature as the amino acid (such as substitution between basic amino acids, substitution between acid amino acids, substitution between polar amino acids, substitution between hydrophobic amino acids, substitution between aromatic amino acids) in a protein, the proteins before the substitution generally has often the same nature as the proteins after the substitution.

The identity in the above each protein is 90% or more as described above, and preferably 93% or more, more preferably 95% or more, still preferably 97% or more, still more preferably 98% or more, and among others preferably 99% or more. The identity of the amino acid sequences can be determined by using algorism such as BLAST or FASTA and setting an appropriate search condition.

The polynucleotide of the present invention is a polynucleotide encoding the protein having the immunogenicity of the cedar pollen allergen protein.

Example of the polynucleotide may include DNA, RNA, and PNA. DNA is preferable among them. The origin of the polynucleotide and the method for producing the polynucleotide are not particularly limited, and the polynucleotide may be a native polynucleotide, a recombinant polynucleotide, or a polynucleotide obtained by chemical synthesis.

Examples of the polynucleotide encoding the protein having the immunogenicity of the cedar pollen may include polynucleotides encoding any one of the above proteins (A) to (C). Specific examples may include following (a), (b), and (c).

(a) The polynucleotide encoding the amino acid sequence represented by SEQ ID NO:1.

(b) The polynucleotide encoding the protein comprising the amino acid sequence having one or several amino acid substitutions, deletions, insertions, and/or additions in the amino acid sequence represented by SEQ ID NO:1 and having the immunogenicity of the cedar pollen.

(c) The polynucleotide encoding the protein comprising the amino acid sequence having 90% or more identity to the amino acid sequence represented by SEQ ID NO:1 and having the immunogenicity of the cedar pollen.

Examples of the polynucleotide encoding the protein having the immunogenicity of the cedar pollen may also include polynucleotides encoding any one of the above proteins (D) to (F). Specific examples may include following polynucleotides (d), (e), and (f).

(d) The polynucleotide encoding the amino acid sequence represented by any one of SEQ ID NOS:2 to 4.

(e) The polynucleotide encoding the protein comprising the amino acid sequence having one or several amino acid substitutions, deletions, insertions, and/or additions in the amino acid sequence represented by any one of SEQ ID NOS:2 to 4 and having the immunogenicity of the cedar pollen.

(f) The polynucleotide encoding the protein comprising the amino acid sequence having 90% or more identity to the amino acid sequence represented by any one of SEQ ID NOS:2 to 4 and having the immunogenicity of the cedar pollen.

Examples of the polynucleotide encoding the protein having the immunogenicity of the cedar pollen may further include following polynucleotides (g) to (r).

(g) The polynucleotide encoding the protein comprising the amino acid sequence represented by SEQ ID NO:1 and the amino acid sequence represented by any one of SEQ ID NOS:2 to 4.

(h) The polynucleotide encoding the protein comprising the amino acid sequence represented by SEQ ID NO:1 and the amino acid sequence having one or several amino acid substitutions, deletions, insertions, and/or additions in one or two or more amino acid sequences in the amino acid sequences represented by SEQ ID NOS:2 to 4 and having the immunogenicity of the cedar pollen.

(i) The polynucleotide encoding the protein comprising the amino acid sequence represented by SEQ ID NO:1 and the amino acid sequence having 90% or more identity to one or two or more amino acid sequences in the amino acid sequences represented by SEQ ID NOS:2 to 4 and having the immunogenicity of the cedar pollen.

(j) The polynucleotide encoding the protein comprising the amino acid sequence having one or several amino acid substitutions, deletions, insertions, and/or additions in the amino acid sequence represented by SEQ ID NO:1 and one or two or more amino acid sequences in the amino acid sequences selected from SEQ ID NOS:2 to 4 and having the immunogenicity of the cedar pollen.

(k) The polynucleotide encoding the protein comprising the amino acid sequence having 90% or more identity to the amino acid sequence represented by SEQ ID NO:1 and one or two or more amino acid sequences in the amino acid sequences represented by SEQ ID NOS:2 to 4 and having the immunogenicity of the cedar pollen.

(l) The polynucleotide encoding the protein comprising the amino acid sequence having one or several amino acid substitutions, deletions, insertions, and/or additions in the amino acid sequence represented by SEQ ID NO:1 and the amino acid sequence having one or several amino acid substitutions, deletions, insertions, and/or additions in one or two or more amino acid sequences in the amino acid sequences represented by SEQ ID NOS:2 to 4 and having the immunogenicity of the cedar pollen.

(m) The polynucleotide encoding the protein comprising the amino acid sequence having 90% or more identity to the amino acid sequence represented by SEQ ID NO:1 and the amino acid sequence having 90% or more identity to one or two or more amino acid sequences in the amino acid sequences represented by SEQ ID NOS:2 to 4 and having the immunogenicity of the cedar pollen.

(n) The polynucleotide encoding the protein comprising the amino acid sequence having 90% or more identity to the amino acid sequence represented by SEQ ID NO:1 and the amino acid sequence having one or several amino acid substitutions, deletions, insertions, and/or additions in one or two or more amino acid sequences in the amino acid sequences represented by SEQ ID NOS:2 to 4 and having the immunogenicity of the cedar pollen.

(o) The polynucleotide encoding the protein comprising the amino acid sequence having one or several amino acid substitutions, deletions, insertions, and/or additions in the amino acid sequence represented by SEQ ID NO:1 and the amino acid sequence having 90% or more identity to one or two or more amino acid sequences in the amino acid sequences represented by SEQ ID NOS:2 to 4 and having the immunogenicity of the cedar pollen.

Meanwhile, examples of the polynucleotide encoding the protein having the immunogenicity of the cedar pollen may include following polynucleotides (p) to (r) in terms of nucleotide sequence.

(p) The polynucleotide comprising a nucleotide sequence represented by SEQ ID NO:5.

(q) The polynucleotide comprising a nucleotide sequence represented by any one of SEQ ID NOS:6 to 8.

(r) The polynucleotide comprising the nucleotide sequence represented by SEQ ID NO:5 and the nucleotide sequence represented by any one of SEQ ID NOS:6 to 8.

The nucleotide sequence represented by SEQ ID NO:5 contains "atggga" encoding "Met-Gly" from the $1^{st}$ nucleotide position to the $6^{th}$ nucleotide position and these six nucleotides were artificially introduced to confer a start codon, atg. The nucleotide sequence represented by SEQ ID NO:5 from the $7^{th}$ nucleotide position to the $1164^{th}$ nucleotide position corresponds to the amino acid sequence represented by SEQ ID NO:1 when translated. The nucleotide sequences represented by SEQ ID NOS:6 to 8 correspond to the amino acid sequences represented by SEQ ID NOS:2 to 4, respectively.

The polynucleotide encoding the protein having the immunogenicity of the cedar pollen includes all polynucleotides that express the protein having the immunogenicity of the cedar pollen even if it does not comprise the nucleotide sequence itself represented by SEQ ID NO:5 and the nucleotide sequence itself represented by SEQ ID NOS:6 to 8. Examples of the polynucleotide encoding the protein having the immunogenicity of the cedar pollen may include following polynucleotides (s) to (z).

(s) The polynucleotide that hybridizes with a polynucleotide composed of a nucleotide sequence complementary to the nucleotide sequence represented by SEQ ID NO:5 under a stringent condition.

(t) The polynucleotide comprising a nucleotide sequence having 90% or more identity to the nucleotide sequence represented by SEQ ID NO:5.

(u) The polynucleotide comprising a nucleotide sequence having one or several nucleotide substitutions, deletions, insertions, and/or additions in the nucleotide sequence represented by SEQ ID NO:5.

(v) The polynucleotide that hybridizes with a polynucleotide composed of a nucleotide sequence complementary to the nucleotide sequence represented by any one of SEQ ID NOS:6 to 8 under the stringent condition.

(w) The polynucleotide comprising a nucleotide sequence having 90% or more identity to the nucleotide sequence represented by any one of SEQ ID NOS:6 to 8.

(x) The polynucleotide comprising a nucleotide sequence having one or several nucleotide substitutions, deletions, insertions, and/or additions in the nucleotide sequence represented by any one of SEQ ID NOS:6 to 8.

(y) The polynucleotide having the nucleotide sequence comprising the mutation of any one of above (s), (t) and (u) in the nucleotide sequence represented by SEQ ID NO:5 and the nucleotide sequence represented by any one of SEQ ID NOS:6 to 8.

(z) The polynucleotide having the nucleotide sequence represented by SEQ ID NO:5 and the nucleotide sequence comprising the mutation of any one of above (v), (w) and (x) in the nucleotide sequence represented by any one of SEQ ID NOS:6 to 8.

The stringent condition in the above polynucleotide refers to the condition where a specific hybrid is formed whereas a non-specific hybrid is not formed. Examples of the stringent condition may include a washing condition (Example 1) with 5×SSC (sodium chloride/sodium citrate) and 0.1% SDS at 42° C., a washing condition (example 2) with 5×SSC and 0.1% SDS (sodium dodecyl sulfate) at 50° C., and a washing condition (example 3) with 5×SSC and 0.1% SDS at 65° C. in washing after the hybridization. The (Example 2) or (example 3) are preferable and the (example 3) is more preferable among them.

The number of the substituted, deleted, inserted, and/or added nucleotides in the above polynucleotide is one or several, and typically 1 to 15, for example, 1 to 10 or 1 to 7, preferably 1 to 5, and more preferably 1 to 3. The identity in the above polynucleotide is 90% or more, and preferably 93% or more, more preferably 95% or more, still preferably 97% or more, still more preferably 98% or more, and among others preferably 99% or more. The identity of the nucleotide sequences can be determined by using algorism such as BLAST or FASTA and setting an appropriate search condition.

The method for acquiring the polynucleotide is not particularly limited, and the polynucleotide can be isolated from organisms or the like utilizing the publicly known technology based on a portion of the amino acid sequence of the protein having the immunogenicity of the cedar pollen or a portion of the nucleotide sequence of the polynucleotide of the present invention. Examples of the publicly known technology may include cloning, gene recombination, PCR, hybridization, site-directed mutagenesis, treatment with a mutagen, and treatment with a restriction enzyme. The nucleotide sequence of the polynucleotide of the present invention may be made artificially. Further, the polynucleotide may be produced using a transformant described later.

The protein having the immunogenicity of the cedar pollen can be expressed in various organisms. The method for expressing the protein in the organism is not particularly limited, and a factor controlling the expression of the polypeptide can be utilized. Examples of the factor controlling the expression of the polypeptide may include promoters, terminators, and signal sequences are exemplified.

The promoter may be a promoter capable of being expressed in a host. Among them, the promoter capable of being expressed in a plant (e.g., gramineous plant) is preferable, among others the promoter capable of being expressed in storage tissue of a seed (seed specific promoter) is more preferable, the promoter expressed in rice (rice seed) is more preferable, and the promoter expressed specifically in rice (rice seed) is still more preferable. Examples of the seed specific promoter may include promoters for genes of seed storage proteins, such as glutelin, prolamine, and globulin. Examples of the glutelin promoter may include GluB1 promoter (e.g., having the nucleotide sequence represented by SEQ ID NO:11) and GluB4 promoter (e.g., having the nucleotide sequence represented by SEQ ID NO:12). Examples of the prolamine promoter may include 16 kDa prolamine promoter (e.g., having the nucleotide sequence represented by SEQ ID NO:13) and 10 kDa prolamine promoter (e.g., having the nucleotide sequence represented by SEQ ID NO:14). However, the promoter capable of being used in the present invention is not limited to the above seed specific promoters, and promoters other than them, such as plant virus-derived promoters may also be used.

The terminator may be a terminator capable of being expressed in the host. Among them, the terminator capable of being expressed in the plant (e.g., gramineous plant) is preferable, among others the terminator capable of being expressed in the storage tissue of the seed is more preferable, the terminator expressed in the rice (*Oryza sativa* seed) is more preferable, and the terminator expressed specifically in rice (rice seed) is still more preferable. When the polypeptide is expressed in a rice plant, examples of the terminator which can be used may include 0.6 kb GluB1 terminator (e.g., having the nucleotide sequence represented by SEQ ID NO:18) and GluB4 terminator (e.g., having the nucleotide sequence represented by SEQ ID NO:19) for glutelin that is a plant seed storage protein, 10 kDa prolamine terminator (e.g., having the nucleotide sequence represented by SEQ ID NO:21), 16 kDa prolamine terminator (e.g., having the nucleotide sequence represented by SEQ ID NO:20), and globulin terminator. The terminators for plant genes registered in DNA database, such as the terminator for nopaline synthetase and the terminator for octopine synthetase, maybe also selected and used.

The polynucleotide encoding the signal sequence is not particularly limited as long as it is expressed in a cell of the host, and may be added to either a 5' terminus or a 3' terminus of the polynucleotide to be expressed. Among them, the signal sequence capable of being expressed in the plant (e.g., gramineous plant) is preferable, among others the signal sequence capable of being expressed in the storage tissue of the seed is preferable, the signal sequence expressed in the rice (rice seed) is more preferable, and the signal sequence expressed specifically in the rice (rice seed) is still more preferable. Example of the signal sequences which can be used may be include the signal sequences shown as examples in JP 2004-321079-A. Among them, a storage protein signal and an endoplasmic reticulum retention signal (e.g., Lys-Asp-Glu-Leu) are preferable. The storage protein signal sequence has a function to transfer the protein of the present invention to the endoplasmic reticulum. The endoplasmic reticulum retention signal sequence has a function to increase an amount of the accumulated protein of the present invention in a storage site of the seed.

The method for expressing the protein having the immunogenicity of the cedar pollen is not particularly limited, and the method of using a vector comprising the polynucleotide encoding the protein having the immunogenicity of the cedar pollen is preferable. The vector can be selected from various vectors known publicly appropriately in consideration of the type of the plant in which the protein is expressed, and is not particularly limited as long as the present genetic constitution is kept stable. A target polynucleotide can be inserted into the vector according to standard methods such as a ligase reaction using restriction enzyme sites. The vector may include, if necessary, expression controlling factors such as a promoter, a terminator, an enhancer, a splicing signal, a poly A addition signal, a ribosome binding site and a replication origin, and a selection marker gene in addition to the target polynucleotide. The promoter and the terminator are generally inserted in a 5' terminal side and a 3' terminal side of the polynucleotide, respectively.

Examples of the selection marker gene may include a hygromycin phosphotransferase gene that imparts resistance to a hygromycin that is an antibiotic, a neomycin phosphotransferase gene that imparts the resistance to kanamycin or gentamicin, an acetyltransferase gene that imparts the resistance to phosphinothricin that is a herbicide, and a mutated acetolactate synthase (mALS) gene that imparts the resistance to Pyriminobac that is a herbicide. By the use of the vector in which the selection marker gene has been introduced, it becomes easy to select a sample in which the target polynucleotide has been introduced.

The polynucleotide encoding the protein having the immunogenicity of the cedar pollen may be inserted into the vector together with a polynucleotide encoding another protein. This can express a fusion protein including the target protein when the vector is transformed, and can control an expression site and an expression amount depending on the selection of the other protein. When the host of the transformation is the rice plant, the protein that is highly and stably expressed in the rice seed is preferable as the other protein, and glutelin is more preferable. The method for inserting the target polynucleotide together with the polynucleotide encoding the other protein is not particularly limited, and examples of the method may include a method that a site to which any DNA sequence can be inserted (e.g., Cfr9I site when the other protein is glutelin) is previously added to a variable region of the other protein, and the target polypeptide is inserted utilizing this site.

As the method for expressing the protein having the immunogenicity of the cedar pollen, it is preferable to utilize a transformant in which the vector containing the polynucleotide encoding the protein having the immunogenicity of the cedar pollen has been introduced. This can efficiently obtain a gene recombinant body (e.g., a gene recombinant plant, preferably a gene recombinant rice plant) in which the protein having the immunogenicity of the cedar pollen is expressed. This can efficiently replicate the protein having the immunogenicity of the cedar pollen, leading to large-scale production thereof. Further, the vector is easily stored.

The method for making the transformant is not particularly limited, and examples of the method may include a method that the vector is introduced into a host cell, if necessary, together with an expression regulatory factor. The method for inserting the vector into a host tissue or a host cell is not particularly limited. Several methods, such as a method of introducing a vector into a protoplast by polyethylene glycol, a method of introducing a vector into a protoplast by electric pulse, a method of directly introducing a vector into a cell by a particle gun method, a DEAE dextran method, a calcium phosphate method, and a method of introducing the vector through *Agrobacterium*, have been already established, and widely used in the art. Any of them can also be utilized in the present invention.

A host into which the vector is introduced is not particularly limited, and can be selected appropriately as needed.

When the transformant is made for the purpose of producing the plant body having the immunogenicity of the cedar pollen, for one example, any plant capable of being regenerated to a plant body may be available for a host. Examples of the plant parts may include plant organs such as leaves, roots, stems, flowers, and blastodiscs in seeds; plant cells that compose the plant organ; plant tissues such as bundles; cultured plant cells such as calluses and suspension cultured cells. However the plant parts are not limited to them. A plant species of the plant body is not also particularly limited, edible plants are preferable, and cells of the gramineous plants are more preferable. Examples of the gramineous plant may be the rice plant (*Oryza sativa*).

When the transformant is made for the purpose of storage and replication of the vector, for anther example, a host is not necessary to be the plant. Examples of the host may include *Escherichia coli*, yeast, animal cells, and the like.

When the transformation is performed using the vector in which the selection marker gene has been introduced, the selection of the transformant can become easy by placing and culturing the host cell in which the vector has been introduced in known medium for selection containing an appropriate drug for the selection depending on the type of the marker gene introduced together with the vector. Even if the selection marker gene is introduced, a plasmid vector in which the selection marker gene has been introduced is prepared separately from the vector in which the polynucleotide has been introduced, and the plasmid vector is introduced into the host cell. Therefore, the same selection can become possible.

A plant body capable of expressing the protein having the immunogenicity of the cedar pollen can be made by making a vector containing the polynucleotide encoding the protein having the immunogenicity of the cedar pollen, introducing the vector into the plant organ, the plant tissue, or the plant cell as the host cell to obtain a transformant, and growing (regenerating) this transformant to the plant body. The plant body can be grown (regenerated) by known methods depending on the type of the plant cell.

If a plant body in a first generation can be obtained from the transformant, the plant body is grown and is made to reproduce sexually or asexually, and thus the plant body as progenies capable of expressing the protein of the present invention can be obtained. It is also possible to obtain a reproductive material (e.g., seed, fruit, cut ear, tuber, root tuber, stock, callus, protoplast) from any of the transformant, its progenies, and clones thereof, further produce the plant body capable of expressing the protein having the immunogenicity of the cedar pollen based on them, and produce it on a large scale.

The protein having the immunogenicity of the cedar pollen, the transformant containing the polynucleotide encoding the same, and the plant body in which the protein having the immunogenicity of the cedar pollen has been introduced are useful as an active ingredient of the therapeutic agent or the prophylactic agent for the cedar pollinosis targeting the patients with cedar pollinosis or so-called potential patients with cedar pollinosis in mammals including human beings. A dose per day, a dosing method, and a dosage form of the therapeutic agent or the prophylactic agent for the cedar pollinosis are not particularly limited, and can be appropriately determined based on conditions such as a physical condition, a sex, and a body size of a subject. The therapeutic agent or the prophylactic agent for the cedar pollinosis of the present invention can be utilized as pharmaceuticals, quasi drugs, foods, feedstuffs for animals (experimental animals, pet animals). The protein having the immunogenicity of the cedar pollen, the transformant containing the polynucleotide encoding the same, and the plant body in which the protein having the immunogenicity of the cedar pollen has been introduced can also be used suitably in a so-called peptide immunotherapy for the patients with pollinosis in the mammals including the human beings. That is, the pollinosis can be treated or prevented by administering the protein having the immunogenicity of the cedar pollen, the transformant containing the polynucleotide encoding the same, and the plant body in which the protein having the immunogenicity of the cedar pollen has been introduced, to the mammals including the human beings.

EXAMPLES

The present invention will be more specifically described with reference to following Examples, however the present invention is not limited to such Examples. Detailed experimental manipulations of molecular biological techniques in following Examples were performed according to Molecular Cloning (Sambrook et. al., 1989) or instructions of reagent manufacturers unless otherwise set forth specifically. Detailed experimental manipulations of immunological techniques targeting mice and samples derived from the mice were performed according to Cell Technology Supplement, Mouse Anatomy Illustrated (Shujunsha), Biochemical Experimental Methods 50, Experimental Methods for Intestinal Cell Functions (Japan Scientific Societies Press), or instructions of reagent manufacturers unless otherwise written specifically.

Example 1

I. Production of Plasmid pCSPmALS Cryj1Cryj2

In order to produce an objective binary vector, a destination binary vector (pCSPmALS 43GW) derived from pPZP200 was produced, which ligates a mutated acetolactate synthase gene (mALS, Kumiai Chemical Industry Co., Ltd.) to a callus-specific promoter (CSP, Kumiai Chemical Industry Co., Ltd.). The destination binary vector (pCSPmALS 43GW) comprises a selection marker gene cassette ligating a 10 kDa prolamine terminator downstream thereof, and comprises attR4-attR3 in a transfer DNA (T-DNA) region.

A special entry clone was made in order to insert a gene cassette into pCSPmALS 43GW. That is, a DNA fragment composed of an attachment region of three combinations of following (1) to (3) and an original multicloning site (SEQ ID NO:9) was inserted sequentially into BssHII site located on both ends of a multicloning site of pBluescript KS+ plasmid (SEQ ID NO:10), and each was designated as pKS4-1 MCS II, pKS221 MCS II, and pKS2-3 MCS II, respectively.

```
Attachment region (1):
attL4-AscI-HindIII-XbaI-BamHI-EcoRV-SmaI-KpnI-

SacI-EcoRI-MluI-attR1

Attachment region (2):
attL1-AscI-HindIII-XbaI-BamHI-EcoRV-SmaI-KpnI-

SacI-EcoRI-MluI-attL2

Attachment region (3):
attR2-AscI-HindIII-XbaI-BamHI-EcoRV-SmaI-KpnI-

SacI-EcoRI-MluI-attL3)
```

The products from Invitrogen were used as above attL1, attL2, attL3, attL4, attR1, and attR2.

A gene cassette composed by combining three types of albumen-specific promoters [10 kDa prolamine promoter (SEQ ID NO:14), GluB4 promoter (SEQ ID NO:12), and 16 kDa prolamine promoter (SEQ ID NO:13)], a coding region each of a seed storage protein glutelin [GluA2 (SEQ ID NO:15), GluB1 (SEQ ID NO:16), GluC (SEQ ID NO:17)] to which a Cfr9I site had been previously added so that any DNA sequence could be inserted into a variable region, and terminators [10 kDa prolamine terminator (SEQ ID NO:21), GluB4 terminator (SEQ ID NO:19), and 16 kDa prolamine terminator (SEQ ID NO:20)] was inserted into pKS4-1 MCS II, pKS221 MCS II, and pKS2-3 MCS II, respectively. That is, the plasmid pKS4-1 was obtained, in which the gene cassette composed of the 10 kDa prolamine promoter, the GluB1 coding region, and the 10 kDa prolamine terminator had been inserted. The plasmid pKS221 was also obtained, in which the gene cassette composed of the GluB4 promoter, the GluA2 coding region, and the GluB4 terminator had been inserted. Further the plasmid pKS2-3 was obtained, in which the gene cassette composed of the 16 kDa prolamine promoter, the GluC coding region, and the 16 kDa prolamine terminator had been inserted.

A polynucleotide composed of a nucleotide sequence represented by SEQ ID NO:6 (corresponds to an amino acid sequence represented by SEQ ID NO:2) was inserted into the Cfr9I site in the GluA2 coding region of pKS221. The resulting gene cassette composed of the GluB4 promoter, the GluA2 coding region (including the polynucleotide composed of the nucleotide sequence represented by SEQ ID NO:6), and the GluB4 terminator included in pKS221 was designated as a Cryj1 F1 expression gene cassette.

A polynucleotide composed of a nucleotide sequence represented by SEQ ID NO:7 (corresponds to an amino acid sequence represented by SEQ ID NO:3) was inserted into the Cfr9I site in the GluB1 coding region of pKS4-1. The resulting gene cassette composed of the 10 kDa prolamine promoter, the GluB1 coding region (including the polynucleotide composed of the nucleotide sequence represented by SEQ ID NO:7), and the 10 kDa prolamine terminator included in pKS4-1 was designated as a Cryj1 F2 expression gene cassette.

A polynucleotide composed of a nucleotide sequence represented by SEQ ID NO:8 (corresponds to an amino acid sequence represented by SEQ ID NO:4) was inserted into the Cfr9I site in the GluC coding region of pKS2-3. The resulting gene cassette composed of the 16 kDa prolamine promoter, the GluC coding region, and the 16 kDa prolamine terminator included in pKS2-3 was designated as a Cryj1 F3 expression gene cassette. The Cryj1 F1 expression gene cassette, the Cryj1 F2 expression gene cassette, and the Cryj1 F3 expression gene cassette were ligated to designate as a Cryj1 full-length expression gene cassette group.

Meanwhile, a polynucleotide encoding Lys-Asp-Glu-Leu that was an endoplasmic reticulum retention signal was added to a C terminus of a polynucleotide (SEQ ID NO:5) encoding a polypeptide composed of an amino acid sequence represented by SEQ ID NO:1 to obtain a polynucleotide. The GluB1 promoter (SEQ ID NO:11) was ligated to a 5' side of this polynucleotide, and KDEL sequence and the GluB1 terminator (SEQ ID NO:18) were ligated to a 3' side of this polynucleotide. The resulting gene cassette was designated as a Cryj2 full-length expression gene cassette. Subsequently, the Cryj2 full-length expression gene cassette was inserted into MluI site of pKS2-3 having the Cryj1 F3 expression gene cassette.

An LR reaction was carried out according to the instructions of Gateway (registered trademark) system (Invitrogen). First, three entry clones, i.e., pKS4-1 comprising the Cryj1 F2 expression gene cassette, pSK221 comprising the Cryj1 F1 expression gene cassette, and pKS2-3 comprising the Cryj1 F3 expression gene cassette and the Cryj2 full-length expression cassette were adjusted to a concentration of 10 ng/μL. Using them, the LR reaction was performed at 25° C. for 16 hours using LR clonase plus enzyme Mix II from Invitrogen. A reaction solution contained 10 ng of each entry clone, 100 ng of a destination binary vector (CSP:mALS:10 kDa Ter gene cassette had been inserted in place of nucleotide numbers 8794 to 10327 in a nucleotide sequence represented by SEQ ID NO:22), 2 μL of LP clonase plus enzyme Mix II, and TE buffer in total 10 μL. After completing the reaction, 2 μg of proteinase K was added, and the reaction solution was left stand at 37° C. for 10 minutes.

After completing the LR reaction, *Escherichia coli* DH5α strain (TOYOBO, competent high) was transformed with the resulting expression clone. An objective clone, i.e., a binary vector in which the above four gene cassettes had been introduced was selected from resulting *Escherichia coli* colony group. Efficiency of the LR reaction was extremely high, and most colonies were shown to potentially positive in a primary screening by colony PCR. A candidate clone was finally confirmed by sequencing using ABI DNA sequencer Genetic Analyzer 3130, and this was designated as pCSPmALS Cryj1Cryj2.

II. Introduction of pCSPmALS Cryj1Cryj2 into *Agrobacterium*

*Agrobacterium tumefaciens* (*A. tumefaciens*) EHA105 strain was inoculated in 10 mL of YEB liquid medium (5 g/L of beef extract, 1 g/L of yeast extract, 5 g/L of peptone, 5 g/L of sucrose, 2 mM $MgSO_4$, pH 7.2 at 22° C. (hereinafter pH at 22° C. unless otherwise specified)), and cultured at 28° C. until a value at OD630 reached the range of 0.4 to 0.6. The cultured medium was centrifuged at 6900×g at 4° C. for 10 minutes to collect microbial cells, which were then suspended in 20 mL of 10 mM HEPES (pH 8.0) and centrifuged again at 6900×g at 4° C. for 10 minutes to collect the microbial cells. Then, the collected microbial cells were suspended in 200 μL of the YEB liquid medium to use as a bacterial suspension for introduction of a plasmid.

In a 0.5 mL tube, 50 μL of the bacterial suspension for introduction of the plasmid and 3 μL of the plasmid pCSPmALS Cryj1Cryj2 were mixed, and the plasmid was introduced into this mixture using an electroporation method (Gene Pulser II System (BIORAD)). Then, 200 μL of YEB liquid medium was added thereto, and the microbial cells were cultured with shaking at 25° C. for one hour. These microbial cells were seeded onto YEB agar medium (1.5% w/v agar, others were the same as above) supplemented with 100 mg/L of spectinomycin, cultured at 28° C. for two days to obtain a bacterial colony. This bacterial colony was transferred to the YEB liquid medium and further cultured. Subsequently, the plasmid was extracted from the bacterial colony by an alkali method and it was confirmed that the plasmid pCSPmALS Cryj1Cryj2 was introduced into *A. tumefaciens* EHA105 strain. This bacterial colony was designated as *Agrobacterium* EHA105 (pCSPmALS Cryj1Cryj2).

III. Preparation of Material to be Infected

A rice cultivar "Koshihikari strain a123" was used as a subject for gene introduction, and its fully-ripened seeds were sterilized according to a method described in "Experimental Protocol for Model Plants" in Cell Technology Additional Volume, Plant Cell Technology Series 4 (p93-98). The sterilized fully-ripened seeds were placed on N6Cl2 medium (N6 inorganic salts and vitamins, 30 g/L of sucrose, 2.8 g/L of proline, 0.3 g/L of casamino acid, 2 mg/L of 2,4-D, 4 g/L of Gelrite, pH=5.8), sealed with a surgical tape, cultured in a light place at 28° C. and germinated to obtain germinated seeds. This germinated seed was used as the material to be infected with *Agrobacterium* EHA105 (pCSPmALS Cryj1Cryj2) in following IV.

IV. Transformation of Rice Plant with EHA105 (pCSPmALS Cryj1Cryj2) and Production of Transformed Rice Plant

*Agrobacterium* EHA105 (pCSPmALS Cryj1Cryj2) cultured on YEB agar medium (5 g/L of beef extract, 1 g/L of yeast extract, 5 g/L of peptone, 5 g/L of sucrose, 2 mM $MgSO_4$, 15 g/L of agar) was further cultured in the YEB medium at 25° C. at 180 rpm overnight, and subsequently centrifuged at 3000 rpm for 20 minutes to collect microbial cells. The microbial cells were suspended at a density of $OD_{630}$=0.15 in N6 liquid medium (N6 inorganic salts and vitamins, Chu C. C., 1978, Proc. Symp. Plant Tissue Culture, Science Press Peking, pp. 43-50), 30 g/L of sucrose, 2 mg/L of 2,4-D, pH=5.8) containing acetosyringone (10 mg/L) to use as an *Agrobacterium* suspension for the infection.

The germinated seeds prepared in III above were placed into a 50 mL tube, and the *Agrobacterium* suspension for the infection was poured thereto to immerse the germinated seeds. After the immersion for 1.5 minutes, the *Agrobacterium* suspension was discarded, and the germinated seeds were placed on sterilized filter paper to remove extra moisture. Subsequently, the germinated seeds were placed on N6Cl2 medium (N6 inorganic salts and vitamins, 30 g/L of sucrose, 2.8 g/L of proline, 0.3 g/L of casamino acid, 2 mg/L of 2,4-dichlorophenoxyacetic acid (2,4-D), 4 g/L of Gelrite, pH=5.2) that is a cocultivation medium, sealed with the surgical tape, and cultured in a dark place at 28° C. for 3 days. Subsequently, the co-cultured germinated seeds were cultured in an N6Cl2TCH25 medium (N6 inorganic salts and vitamins, 30 g/L of sucrose, 2.8 g/L of proline, 0.3 g/L of casamino acids, 2 mg/L of 2,4-D, 400 mg/L of carbenicillin, 1 μM Pyriminobac, 4 g/L of Gelrite) for one week, and then a germinated bud was cut out from scutellum tissue.

Then, this bud was cultured on an N6Cl4TCH25 medium (N6 inorganic salts and vitamins, 30 g/L of sucrose, 2.8 g/L of proline, 0.3 g/L of casamino acids, 4 mg/L of 2,4-D, 400 mg/L of carbenicillin, 1 μM Pyriminobac, 4 g/L of Gelrite) for one week, and further cultured on an MSRC medium (MS inorganic salts and vitamins (Murashige, T. and Skoog, F., 1962 Physiol. Plant., 15, 473), 30 g/L of sucrose, 30 g/L of sorbitol, 2 g/L of casamino acids, 1 μg/mL of naphthalene acetic acid (NAA), 2 μg/mL of benzyl aminopurine (BAP), 400 mg/L of carbenicillin, 4 g/L of Gelrite).

As described above, the bud or a juvenile plant body was regenerated from the infected seed during one to two months after starting the cocultivation of the infected seeds and *Agrobacterium* EHA105 (pCSPmALS Cryj1Cryj2). The regenerated bud or juvenile plant body was implanted in a rooting medium and grown therein to obtain a young seedling having a height of about 20 cm. Chromosomal DNA was extracted from this young seedling and the presence of the Cryj1Cryj2 gene in the young seedling was identified by southern hybridization.

V. Production of Recombinant Rice Plant on Large Scale

The germinated seeds of the rice plant that was the transformant (Tg rice plant) obtained in IV above were seeded on urethane and subsequently raised in a seedling raising room (artificial sunlight room) in a special isolation chamber to obtain a seedling. That is, 49 seedlings per panel were planted in all regions of beds, and about 12,000 seedlings per unit were planted.

Five hydroponic beds (supplied from M Hydroponic Research Co., Ltd., H: 73 cm×W: 120 cm×D: 2,900 cm) per unit were arranged in a cultivation unit in the special isolation chamber. Nutrient solution pipings of the respective hydroponic beds were connected into one pipe and a hydroponic nutrient solution is circulated among the hydroponic beds by a circulating pump. Thus, a composition of the nutrient solution is the same in the respective hydroponic beds. Various sensors (pH meter, electric conductivity (EC) meter, water temperature meter) are available in the hydroponic bed, and their data were automatically saved every 10 minutes in an environmental control personal computer (PC). Fertilization and addition of a pH adjuster are controlled by a nutrient solution controller. Various conditions (pH, EC and water temperature) in the hydroponic bed can be automatically controlled by the sensors, the environmental control personal computer and the solution controller.

Concerning fertilizers, commercially available fertilizers specific for hydroponic cultivation (M1: 7% nitrate nitrogen, 3% ammonium nitrogen, 8% water-soluble phosphoric acid, 23% water-soluble potassium, 4% water-soluble magnesium, 0.1% water-soluble manganese, 0.1% water-soluble boron; M2: 11% nitrate nitrogen; M5: 6% ammonium nitrogen, 9% water-soluble potassium, 1% water-soluble manganese, 1% water-soluble boron) (supplied from M Hydroponic Research Co., Ltd.) were used based on results of measuring concentrations of the nitrate nitrogen and the ammonium nitrogen in the hydroponic nutrient solution. The temperature of the hydroponic nutrient solution was set at 29° C.

A day length was controlled by the use of a light supplement lamp and a 100% light shielding curtain (long-day environment: 12 hours light and 12 hours dark; and short-day environment: 11 hours light and 13 hours dark). An internal temperature was automatically controlled by open and close of a side window and a skylight window side by an environmental control system. However, for a flowering period, the windows were closed with driving air conditioners for the purpose of preventing scatter of pollens. In this cultivation method, the rice plant was cultivated for 150 days from the seeding to the harvest.

As a result, the presence of the Cryj1 gene and the Cryj2 gene was identified in all individuals germinated from the seeds of the Tg rice plant. Further, rice seeds (rice) harvested from the individual were analyzed, and it was identified that the seed contained total proteins in a mass of 0.1 g/g of rice and comprised the cedar pollen allergy antigen Cryj1 fragmented into three fragments (amino acid sequences represented by SEQ ID NOS:2 to 4) and shuffled Cryj2 (amino acid sequence represented by SEQ ID NO:1).

VI. Induction of Immune Tolerance by Oral Ingestion of Rice Seed in Mice

Male BALB/c mice aged 5 weeks were purchased from Charles River Laboratories Japan Inc., and oral ingestion of the rice seed harvested from the germinated seed of the Tg rice plant in V above (hereinafter, referred to as a "Tg-rice" or "Tg-seed") was started in these mice. First, rice seeds not transformed (hereinafter, referred to as a "Non-Tg rice" or "Non-Tg-seed") and the Tg-seeds (both were unpolished rice derived from fully-ripened seed) were pulverized into fine particles using P-14 rotor speed mill supplied from Fritsch Japan Co., Ltd. at a rotation frequency of about 10,000 rpm to obtain each rice seed powder. Subsequently, the mice were divided into two groups, and each rice seed powder was placed in a diet feeder bottle and was freely digested by the mice in each group for 20 days. After orally administrating the rice seed powder, a total digested amount of the rice seed powder in each group was calculated, and thus estimated to be about 6 g per mouse.

VII. Challenge with Cedar Pollen Allergen

A mixed solution containing 0.1 mg of a cedar pollen extracted protein (code number: LG-5280) supplied from LSL Co., Ltd., 5 mg of alum (aluminium hydroxide gel, code number LG-6000) supplied from LSL Co., Ltd., and 0.1 μg of murine IL-4 (code number: 404-ML) supplied from R & D Systems Inc. per mouse was intraperitoneally administered to all mice that had orally ingested the aforementioned Non-Tg rice seed powder or Tg rice seed powder on the following day of the final oral ingestion day of each rice seed powder. One week after this, a mixed solution containing 0.1 mg of the cedar pollen extracted protein and 5 mg of alum per mouse was intraperitoneally administered to the mice.

VIII. Measurement of T Cell Proliferation Activity and Amounts of Produced Cytokines Two weeks after the second intraperitoneal administration of the mixed solution containing the cedar pollen extracted protein and alum, $CD4^+$ T cells were isolated from spleen of the mouse using CD4 (L3T4) MicroBeads (code number 130-049-201) supplied from Miltenyi Biotec K.K. and autoMACS (trademark) automatic magnetic cell sorter (code number 130-020-101) supplied from Miltenyi Biotec K.K. These $CD4^+$ T cells at $1\times10^5$, antigen presenting cells at $5\times10^5$ prepared from spleen of a naive male BALE/c mouse, and 20 μg/mL of the cedar pollen extracted protein as an antigen were mixed in a 96-well plate for cell culture, and cultured at 37° C. for 5 days.

After completing the cell culture, the number of living cells was determined by a colorimetric assay using CellTiter 96 (registered trade mark) AQueous One Solution Cell Proliferation Assay reagent (code number G3580) supplied from Promega. The proliferative activity of the $CD4^+$ T cells in an experimental group of orally administering the Tg rice seed powder and an experimental group of orally administering the Non-Tg rice seed powder was shown as a stimulation index (S.I.) specific for the cedar pollen allergen in FIG. 1. A ratio of the number of the proliferated cells when the cedar pollen extracted protein that was the antigen was added to the number of the proliferated cells when the cedar pollen extracted protein was not added is represented as the stimulation index (S.I.) specific for the cedar pollen allergen (FIG. 1).

As is evident from the results shown in FIG. 1, the proliferative activity of the T cells by the stimulation with the cedar pollen allergen was significantly inhibited in the group of orally administering the Tg rice seed powder compared with the group of orally administering the Non-Tg rice seed powder ($p<0.01$).

Upon completing the cell culture, a supernatant fraction of the T cell culture was partially collected, and amounts of produced various cytokines were measured using Quantikine ELISA Kit supplied from R & D Systems Inc. The amounts of produced IL-4, IL-5, IL-6, IL-10, IL-13, and IFNγ in the group of orally administering the Tg rice seed powder and the group of orally administering the Non-Tg rice seed powder are shown in FIGS. 2 to 7, respectively.

As a result, the production of the cytokines (IL-4, IL-5, IL-13) that induced a Th2 type immune response such as cedar pollen allergy was remarkably inhibited in the group of orally administering the Tg rice seed powder compared with the group of orally administering the Non-Tg rice seed powder. Further, the production of other cytokines (IL-10, IFN-γ) also tended to be inhibited (FIGS. 2 to 7). The amounts of produced IL-5 (FIG. 3), IL-10 (FIG. 5), and IFN-γ (FIG. 7) were identified to be significantly different between the experimental groups at $p<0.05$. The amounts of produced IL-4 (FIG. 2) and IL-13 (FIG. 6) were identified to be significantly different between the experimental groups at $p<0.01$.

IX. Measurement of Antibody Specific for Cedar Pollen Allergen and Amount of Produced Histamine Serum was collected from the mice two weeks after the second intraperitoneal administration of the mixed solution containing the cedar pollen extracted protein and alum, and the amount of produced antibody specific for the cedar pollen allergen and the amount of the produced histamine were determined. First, in order to measure the amount of the produced antibody specific for the cedar pollen allergen, an anti-mouse IgE antibody, which was supplied from Southern Biotech and diluted with 50 mM carbonate-bicarbonate buffer (pH 9.6) to 2 μg/mL, and an anti-mouse IgG antibody, which was diluted in the same manner, were each added to each well in a 96-well plate, and left stand at 4° C. overnight. The plate was washed with PBS, and then Block Ace (code number UK-B80) supplied from DS Pharma Biomedical Co., Ltd. was added to the plate to perform blocking at 25° C. for 2 hours.

Subsequently, the serum collected from the mouse was added to each well, reacted at 25° C. for 2 hours, then a biotinylated cedar pollen extracted protein was added to each well, and reacted at 25° C. for 2 hours. Subsequently, horseradish peroxidase (HRP)-labeled streptoavidin (code number N100) supplied from Endogen and diluted to 1/5000 was added to each well, and, reacted at 25° C. for one hour, and then, BD OptEIA solution (code number 550536) supplied from BD Biosciences, which was a substrate of HRP enzyme, was added to each well to develop a color, and a colorimetric intensity was measured using a microplate reader. Histamine ELISA kit (code number 409010) supplied from NEOGEN CORPORATION was used for measuring the amount of produced histamine. The amounts of produced IgE antibody, IgG antibody, and histamine in the experimental group of orally administering the Tg rice seed powder and the experimental group of orally administering the Non-Tg rice seed powder are shown in FIGS. 8 to 10, respectively.

Figure 8:
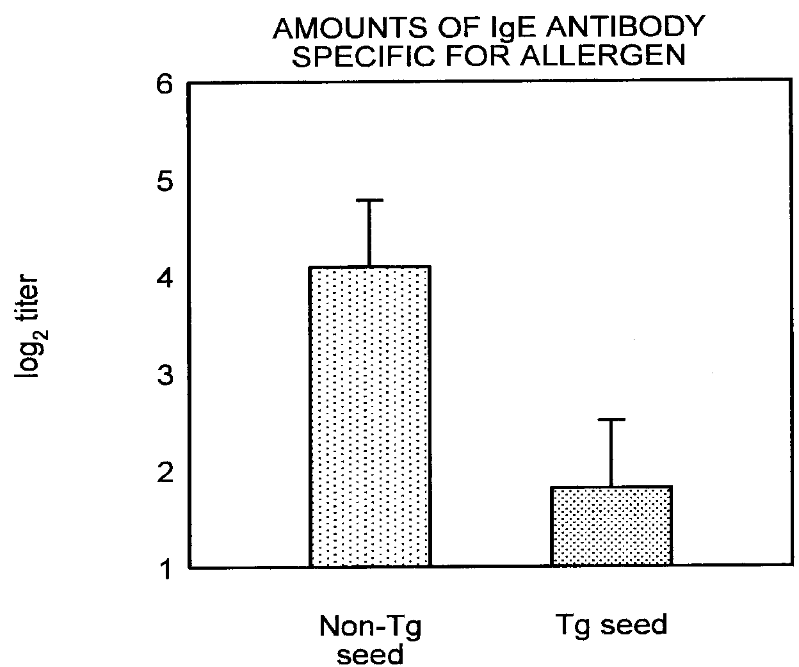
FIG. 8 is a graph showing amounts of an IgE antibody produced in the experimental group of orally administering the Tg rice seeds and the experimental group of orally administering the Non-Tg rice seeds.
Figure 9:
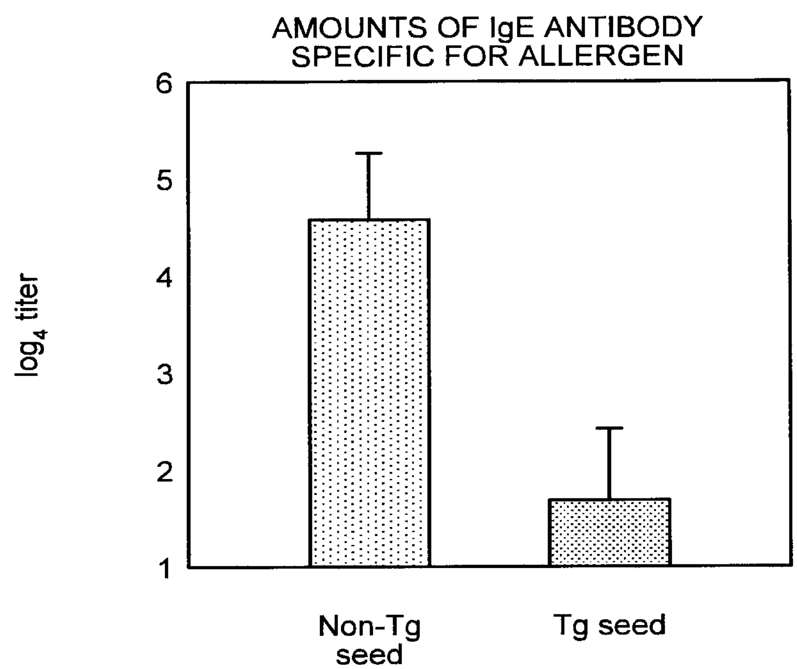
FIG. 9 is a graph showing amounts of an IgG antibody produced in the experimental group of orally administering the Tg rice seeds and the experimental group of orally administering the Non-Tg rice seeds.
Figure 10:
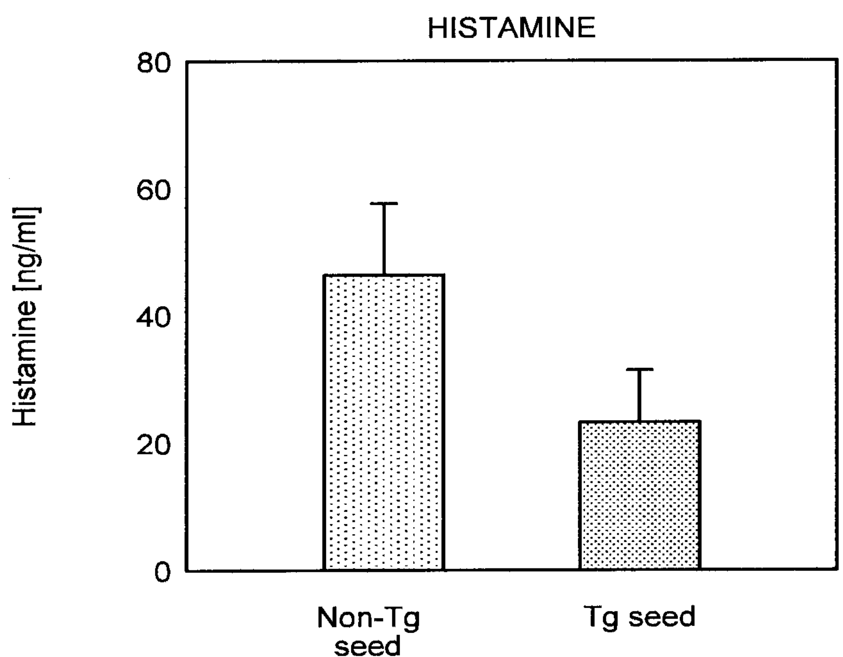
FIG. 10 is a graph showing amounts of histamine produced in the experimental group of orally administering the Tg rice seeds and the experimental group of orally administering the Non-Tg rice seeds.

As a result, the production of the IgE antibody specific for the cedar pollen allergen, the production of the IgG antibody specific for the cedar pollen allergen, and the production of histamine were remarkably inhibited in the experimental group of orally administering the Tg rice seed powder compared with the experimental group of orally administering the Non-Tg rice seed powder (FIGS. 8 to 10).

SEQUENCE LISTING FREE TEXT

SEQ ID NO:1 Amino acid sequence of protein having immunogenicity of cedar pollen allergen (Cryj2) (93 aa-388 aa, 59 aa-92 aa, 1 aa-58 aa)

SEQ ID NO:2 Amino acid sequence of protein having immunogenicity of cedar pollen allergen (Cryj1) (1 aa-144 aa)

SEQ ID NO:3 Amino acid sequence of protein having immunogenicity of cedar pollen allergen (Cryj1) (126 aa-257 aa)

SEQ ID NO:4 Amino acid sequence of protein having immunogenicity of cedar pollen allergen (Cryj1) (231 aa-353 aa)

SEQ ID NO:5 Nucleotide sequence of polynucleotide encoding protein having immunogenicity of cedar pollen allergen (Cryj2)

SEQ ID NO:6 Nucleotide sequence of polynucleotide encoding protein having immunogenicity of cedar pollen allergen (Cryj1)

SEQ ID NO:7 Nucleotide sequence of polynucleotide encoding protein having immunogenicity of cedar pollen allergen (Cryj1)

SEQ ID NO:8 Nucleotide sequence of polynucleotide encoding protein having immunogenicity of cedar pollen allergen (Cryj1)

SEQ ID NO:9 Nucleotide sequence of original multicloning site included in entry clone SEQ ID NO:10 Nucleotide sequence of pBluescript KS+

SEQ ID NO:11 Nucleotide sequence of GluB1 promoter

SEQ ID NO:12 Nucleotide sequence of GluB4 promoter

SEQ ID NO:13 Nucleotide sequence of 16 kDa prolamine promoter

SEQ ID NO:14 Nucleotide sequence of 10 kDa prolamine promoter

SEQ ID NO:15 Nucleotide sequence of GluA2 in which Cfr9I site was internally added SEQ ID NO:16 Nucleotide sequence of GluB1 in which Cfr9I site was internally added SEQ ID NO:17 Nucleotide sequence of GluC in which Cfr9I site was internally added SEQ ID NO:18 Nucleotide sequence of GluB1 terminator SEQ ID NO:19 Nucleotide sequence of GluB4 terminator SEQ ID NO:20 Nucleotide sequence of 16 kDa prolamine terminator SEQ ID NO:21 Nucleotide sequence of 10 kD prolamine terminator SEQ ID NO:22 Nucleotide sequence of destination binary vector

The invention claimed is:

1. A protein selected from the group consisting of:

(A) a protein comprising the amino acid sequence encoded by a polynucleotide comprising the nucleotide sequence represented by SEQ ID NO: 5; and (B) a protein comprising an amino acid sequence having 95% or more identity to the amino acid sequence encoded by a polynucleotide comprising the nucleotide sequence represented by SEQ ID NO: 5, and having immunogenicity to cedar pollen.

2. A polynucleotide selected from the group consisting of:

(a) a polynucleotide comprising the nucleotide sequence represented by SEQ ID NO: 5; and (b) a polynucleotide encoding a protein comprising an amino acid sequence having 95% or more identity to the amino acid sequence encoded by a polynucleotide comprising the nucleotide sequence represented by SEQ ID NO: 5, and having the immunogenicity to the cedar pollen.

3. A vector, comprising the polynucleotide according to claim 2.

4. A transformant in which the vector according to claim 3 has been introduced, wherein said transformant is a microorganism, animal cell, plant, or plant cell.

5. The transformant according to claim 4, wherein said transformant is a plant.

6. The transformant according to claim 4, wherein said transformant is a gramineous plant.

7. A method for producing a protein, the method comprising expressing the polynucleotide of the transformant according to claim 4 and collecting the protein encoded by said expressed polynucleotide.

8. A method for imparting an immunogenicity of a cedar pollen to a plant, the method comprising introducing the polynucleotide according to claim 2 into the plant.

9. A method for producing a plant body having an immunogenicity of a cedar pollen, the method comprising:

introducing a vector comprising the polynucleotide according to claim 2 into a plant organ, a plant tissue, or a plant cell to obtain a transformant; and growing the plant body from said transformant.

10. A therapeutic agent or a prophylactic agent for a cedar pollinosis, comprising the protein according to claim 1 as an active ingredient.

11. A method for treating or preventing a cedar pollinosis, the method comprising administering the protein according to claim 1 to a human in need thereof.

12. A therapeutic agent or a prophylactic agent for a cedar pollinosis, comprising the transformant according to claim 5 as an active ingredient.

13. A method for treating or preventing a cedar pollinosis, the method comprising administering the transformant according to claim 5 to a human in need thereof.

* * * * *

SEQUENCE LISTING

```
<160> NUMBER OF SEQ ID NOS: 22

<210> SEQ ID NO 1
<211> LENGTH: 386
<212> TYPE: PRT
<213> ORGANISM: Artificial
<220> FEATURE:
<223> OTHER INFORMATION: shuffled cryj2

<400> SEQUENCE: 1

Ile Trp Leu Gln Phe Ala Lys Leu Thr Gly Phe Thr Leu Met Gly Lys
1               5                   10                  15

Gly Val Ile Asp Gly Gln Gly Lys Gln Trp Trp Ala Gly Gln Cys Lys
            20                  25                  30

Trp Val Asn Gly Arg Glu Ile Cys Asn Asp Arg Asp Arg Pro Thr Ala
        35                  40                  45

Ile Lys Phe Asp Phe Ser Thr Gly Leu Ile Ile Gln Gly Leu Arg Leu
    50                  55                  60

Met Asn Ser Pro Glu Phe His Leu Val Phe Gly Asn Cys Glu Gly Val
65                  70                  75                  80

Lys Ile Ile Gly Ile Ser Ile Thr Ala Pro Arg Asp Ser Pro Asn Thr
                85                  90                  95

Asp Gly Ile Asp Ile Phe Ala Ser Lys Asn Phe His Leu Gln Lys Asn
            100                 105                 110

Thr Ile Gly Thr Gly Asp Asp Cys Val Ala Ile Gly Thr Gly Ser Ser
        115                 120                 125

Asn Ile Val Ile Glu Asp Leu Ile Cys Gly Pro Gly His Gly Ile Ser
```

-continued

```
    130                 135                 140

Ile Gly Ser Leu Gly Arg Glu Asn Ser Arg Ala Glu Val Ser Tyr Val
145                 150                 155                 160

His Val Asn Gly Ala Lys Phe Ile Asp Thr Gln Asn Gly Leu Arg Ile
                165                 170                 175

Lys Thr Trp Gln Gly Gly Ser Gly Met Ala Ser His Ile Ile Tyr Glu
            180                 185                 190

Asn Val Glu Met Ile Asn Ser Glu Asn Pro Ile Leu Ile Asn Gln Phe
        195                 200                 205

Tyr Cys Thr Ser Ala Ser Ala Cys Gln Asn Gln Arg Ser Ala Val Gln
    210                 215                 220

Ile Gln Asp Val Thr Tyr Lys Asn Ile Arg Gly Thr Ser Ala Thr Ala
225                 230                 235                 240

Ala Ala Ile Gln Leu Lys Cys Ser Asp Ser Met Pro Cys Lys Asp Ile
                245                 250                 255

Lys Leu Ser Asp Ile Ser Leu Lys Leu Thr Ser Gly Lys Ile Ala Ser
            260                 265                 270

Cys Leu Asn Asp Asn Ala Asn Gly Tyr Phe Ser Gly His Val Ile Pro
        275                 280                 285

Ala Cys Lys Asn Leu Ser Asn Asn Leu Phe Phe Asn Gly Pro Cys Gln
    290                 295                 300

Pro His Phe Thr Phe Lys Val Asp Gly Ile Ile Ala Ala Tyr Gln Asn
305                 310                 315                 320

Pro Ala Ser Trp Lys Asn Asn Arg Arg Lys Val Glu His Ser Arg His
                325                 330                 335

Asp Ala Ile Asn Ile Phe Asn Val Glu Lys Tyr Gly Ala Val Gly Asp
            340                 345                 350

Gly Lys His Asp Cys Thr Glu Ala Phe Ser Thr Ala Trp Gln Ala Ala
        355                 360                 365

Cys Lys Lys Pro Ser Ala Met Leu Leu Val Pro Gly Asn Lys Lys Phe
    370                 375                 380

Val Val
385


<210> SEQ ID NO 2
<211> LENGTH: 144
<212> TYPE: PRT
<213> ORGANISM: Cryptomeria japonica

<400> SEQUENCE: 2

Asp Asn Pro Ile Asp Ser Cys Trp Arg Gly Asp Ser Asn Trp Ala Gln
1               5                   10                  15

Asn Arg Met Lys Leu Ala Asp Cys Ala Val Gly Phe Gly Ser Ser Thr
            20                  25                  30

Met Gly Gly Lys Gly Gly Asp Leu Tyr Thr Val Thr Asn Ser Asp Asp
        35                  40                  45

Asp Pro Val Asn Pro Ala Pro Gly Thr Leu Arg Tyr Gly Ala Thr Arg
    50                  55                  60

Asp Arg Pro Leu Trp Ile Ile Phe Ser Gly Asn Met Asn Ile Lys Leu
65                  70                  75                  80

Lys Met Pro Met Tyr Ile Ala Gly Tyr Lys Thr Phe Asp Gly Arg Gly
                85                  90                  95

Ala Gln Val Tyr Ile Gly Asn Gly Gly Pro Cys Val Phe Ile Lys Arg
            100                 105                 110
```

```
Val Ser Asn Val Ile Ile His Gly Leu Tyr Leu Tyr Gly Cys Ser Thr
        115                 120                 125

Ser Val Leu Gly Asn Val Leu Ile Asn Glu Ser Phe Gly Val Glu Pro
    130                 135                 140


<210> SEQ ID NO 3
<211> LENGTH: 132
<212> TYPE: PRT
<213> ORGANISM: Cryptomeria japonica
<220> FEATURE:
<221> NAME/KEY: misc_feature
<222> LOCATION: (21)..(21)
<223> OTHER INFORMATION: Xaa can be any amino acid

<400> SEQUENCE: 3

Cys Ser Thr Ser Val Leu Gly Asn Val Leu Ile Asn Glu Ser Phe Gly
1               5                   10                  15

Val Glu Pro Val Xaa Pro Gln Asp Gly Asp Ala Leu Thr Leu Arg Thr
            20                  25                  30

Ala Thr Asn Ile Trp Ile Asp His Asn Ser Phe Ser Asn Ser Ser Asp
        35                  40                  45

Gly Leu Val Asp Val Thr Leu Thr Ser Thr Gly Val Thr Ile Ser Asn
    50                  55                  60

Asn Leu Phe Phe Asn His His Lys Val Met Leu Leu Gly His Asp Asp
65                  70                  75                  80

Ala Tyr Ser Asp Asp Lys Ser Met Lys Val Thr Val Ala Phe Asn Gln
                85                  90                  95

Phe Gly Pro Asn Cys Gly Gln Arg Met Pro Arg Ala Arg Tyr Gly Leu
            100                 105                 110

Val His Val Ala Asn Asn Asn Tyr Asp Pro Trp Thr Ile Tyr Ala Ile
        115                 120                 125

Gly Gly Ser Ser
    130


<210> SEQ ID NO 4
<211> LENGTH: 123
<212> TYPE: PRT
<213> ORGANISM: Cryptomeria japonica

<400> SEQUENCE: 4

Pro Arg Ala Arg Tyr Gly Leu Val His Val Ala Asn Asn Asn Tyr Asp
1               5                   10                  15

Pro Trp Thr Ile Tyr Ala Ile Gly Gly Ser Ser Asn Pro Thr Ile Leu
            20                  25                  30

Ser Glu Gly Asn Ser Phe Thr Ala Pro Asn Glu Ser Tyr Lys Lys Gln
        35                  40                  45

Val Thr Ile Arg Ile Gly Cys Lys Thr Ser Ser Ser Cys Ser Asn Trp
    50                  55                  60

Val Trp Gln Ser Thr Gln Asp Val Phe Tyr Asn Gly Ala Tyr Phe Val
65                  70                  75                  80

Ser Ser Gly Lys Tyr Glu Gly Gly Asn Ile Tyr Thr Lys Lys Glu Ala
                85                  90                  95

Phe Asn Val Glu Asn Gly Asn Ala Thr Pro Gln Leu Thr Lys Asn Ala
            100                 105                 110

Gly Val Leu Thr Cys Ser Leu Ser Lys Arg Cys
        115                 120


<210> SEQ ID NO 5
```

<211> LENGTH: 1164
<212> TYPE: DNA
<213> ORGANISM: Artificial
<220> FEATURE:
<223> OTHER INFORMATION: shuffled cryj2

<400> SEQUENCE: 5

```
atgggaatct ggctccaatt cgcaaagctc actggcttca cactaatggg aaagggcgtt      60

atcgatggac aaggaaagca gtggtgggct ggacaatgca agtgggtaaa tggccgtgaa     120

atttgcaatg atagggatag acctaccgct atcaagttcg acttcagtac tggactaatt     180

atccaaggcc tcaggcttat gaactctcca gagttccacc tagttttcgg aaattgtgaa     240

ggagttaaga ttatcggaat cagcattaca gcacctcgtg atagcccaaa cactgatggc     300

atcgatattt tcgctagtaa gaatttccat ttgcagaaga acacaattgg aaccggcgat     360

gactgtgtag ctatcggcac tggaagttct aatattgtta tcgaggatct aatctgcggc     420

cctggacacg gcattagtat cggaagcctt ggcagggaaa actctagggc tgaggtaagc     480

tacgttcacg taaatggagc aaagttcatc gatacacaaa acggcctccg tattaagacc     540

tggcaaggcg gaagtggcat ggcatctcat atcatctatg aaaatgttga gatgattaat     600

agcgaaaacc caattctaat caatcagttc tactgtacta gtgcatctgc ttgccaaaac     660

caaagaagcg cagtacagat ccaagatgtt acatataaga atattcgtgg caccagtgct     720

actgctgctg ctatccaact aaagtgtagc gattctatgc cctgcaagga tattaagttg     780

agcgatatca gtctcaagct cacttctgga aagattgcaa gctgtctaaa cgataatgca     840

aatggatact tcagcggcca tgttatcccc gcttgcaaga atcttagtaa caatctattc     900

ttcaatggac catgtcagcc tcatttcaca ttcaaggtag atggcattat tgcagcttat     960

caaaacccag cttcttggaa gaataaccgt agaaaggttg aacacagcag gcatgatgca    1020

atcaatattt tcaacgttga gaagtacggc gcagtaggag atggaaagca cgattgcacc    1080

gaggctttca gtacagcatg gcaagcagct tgcaagaagc catctgcaat gctcttggtt    1140

cccggcaata agaagttcgt tgta                                            1164
```

<210> SEQ ID NO 6
<211> LENGTH: 431
<212> TYPE: DNA
<213> ORGANISM: Cryptomeria japonica

<400> SEQUENCE: 6

```
ataatcccat cgatagctgc tggagaggag atagtaactg ggcacaaaac agaatgaagc      60

tcgcagattg tgcagtgggc ttcggaagct ctactatggg aggcaaggga ggagatcttt     120

atactgttac taactcagat gatgatcctg tgaatcctgc accaggaact ctccgctatg     180

gagcaacccg tgataggccc ctctggatca ttttcagtgg caatatgaat atcaagctca     240

agatgcctat gtacattgct ggctataaga ctttcgatgg caggggagca caagtttata     300

ttggcaatgg cggtccctgt gtgttcatca agagagttag caatgttatc atccacggtt     360

tgtatctcta cggctgtagt actagtgttt tgggcaatgt tttgatcaac gagagtttcg     420

gcgtggagcc t                                                          431
```

<210> SEQ ID NO 7
<211> LENGTH: 396
<212> TYPE: DNA
<213> ORGANISM: Cryptomeria japonica
<220> FEATURE:
<221> NAME/KEY: misc_feature
<222> LOCATION: (63)..(63)
<223> OTHER INFORMATION: n can be any base

<400> SEQUENCE: 7
tgtagtacta gtgttttggg caatgttttg atcaacgaga gtttcggcgt ggagcctgtt 60
cancctcagg atggcgatgc tcttactctc cgcactgcta caaatatttg gattgatcat 120
aattctttct ccaattcttc tgatggtctc gttgatgtta ctcttactag cactggagtt 180
actatttcta acaatctttt cttcaaccat cataaggtga tgttgttggg ccatgatgat 240
gcatatagtg atgataagtc catgaaggtg acagtggcat tcaatcaatt cggacctaac 300
tgtggacaaa gaatgcccag ggcacgttat ggacttgtac atgttgcaaa caataattat 360
gatccctgga ctatctatgc aattggtggc agttca 396

<210> SEQ ID NO 8
<211> LENGTH: 362
<212> TYPE: DNA
<213> ORGANISM: Cryptomeria japonica

<400> SEQUENCE: 8
cacgttatgg acttgtacat gttgcaaaca ataattatga tccctggact atctatgcaa 60
ttggtggcag ttcaaatcca accattctaa gtgaaggcaa tagtttcact gcaccaaatg 120
agagctacaa gaagcaagta accatccgta ttggatgcaa gacaagtagc tcttgttcta 180
attgggtgtg gcaatctaca caagatgttt tctataatgg agcttatttc gtatctagtg 240
gcaagtatga aggcggtaat atctacacaa agaaggaggc tttcaatgtt gagaatggca 300
atgcaactcc tcaattgaca aagaatgctg gcgttttgac atgctctctc tctaagcgtt 360
gt 362

<210> SEQ ID NO 9
<211> LENGTH: 80
<212> TYPE: DNA
<213> ORGANISM: Artificial
<220> FEATURE:
<223> OTHER INFORMATION: multi cloning cite

<400> SEQUENCE: 9
ggcgcgccaa aagcttaatc tagaaaggat ccaagatatc aacccgggaa ggtaccaaga 60
gctcaagaat tcaaacgcgt 80

<210> SEQ ID NO 10
<211> LENGTH: 2961
<212> TYPE: DNA
<213> ORGANISM: Artificial
<220> FEATURE:
<223> OTHER INFORMATION: pBluescript KS+

<400> SEQUENCE: 10
ctaaattgta agcgttaata ttttgttaaa attcgcgtta aatttttgtt aaatcagctc 60
attttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420

-continued

```
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctcta gaactagtgg atcccccggg ctgcaggaat tcgatatcaa    720
gcttatcgat accgtcgacc tcgagggggg gcccggtacc cagcttttgt tccctttagt    780
gagggttaat tgcgcgcttg gcgtaatcat ggtcatagct gtttcctgtg tgaaattgtt    840
atccgctcac aattccacac aacatacgag ccggaagcat aaagtgtaaa gcctggggtg    900
cctaatgagt gagctaactc acattaattg cgttgcgctc actgcccgct ttccagtcgg    960
gaaacctgtc gtgccagctg cattaatgaa tcggccaacg cgcggggaga ggcggtttgc   1020
gtattgggcg ctcttccgct tcctcgctca ctgactcgct gcgctcggtc gttcggctgc   1080
ggcgagcggt atcagctcac tcaaaggcgg taatacggtt atccacagaa tcaggggata   1140
acgcaggaaa gaacatgtga gcaaaaggcc agcaaaaggc caggaaccgt aaaaaggccg   1200
cgttgctggc gtttttccat aggctccgcc cccctgacga gcatcacaaa aatcgacgct   1260
caagtcagag gtggcgaaac ccgacaggac tataaagata ccaggcgttt ccccctggaa   1320
gctccctcgt gcgctctcct gttccgaccc tgccgcttac cggatacctg tccgcctttc   1380
tcccttcggg aagcgtggcg ctttctcata gctcacgctg taggtatctc agttcggtgt   1440
aggtcgttcg ctccaagctg ggctgtgtgc acgaaccccc cgttcagccc gaccgctgcg   1500
ccttatccgg taactatcgt cttgagtcca acccggtaag acacgactta tcgccactgg   1560
cagcagccac tggtaacagg attagcagag cgaggtatgt aggcggtgct acagagttct   1620
tgaagtggtg gcctaactac ggctacacta gaaggacagt atttggtatc tgcgctctgc   1680
tgaagccagt taccttcgga aaaagagttg gtagctcttg atccggcaaa caaaccaccg   1740
ctggtagcgg tggttttttt gtttgcaagc agcagattac gcgcagaaaa aaaggatctc   1800
aagaagatcc tttgatcttt tctacggggt ctgacgctca gtggaacgaa aactcacgtt   1860
aagggatttt ggtcatgaga ttatcaaaaa ggatcttcac ctagatcctt ttaaattaaa   1920
aatgaagttt taaatcaatc taaagtatat atgagtaaac ttggtctgac agttaccaat   1980
gcttaatcag tgaggcacct atctcagcga tctgtctatt tcgttcatcc atagttgcct   2040
gactccccgt cgtgtagata actacgatac gggagggctt accatctggc cccagtgctg   2100
caatgatacc gcgagaccca cgctcaccgg ctccagattt atcagcaata aaccagccag   2160
ccggaagggc cgagcgcaga agtggtcctg caactttatc cgcctccatc cagtctatta   2220
attgttgccg ggaagctaga gtaagtagtt cgccagttaa tagtttgcgc aacgttgttg   2280
ccattgctac aggcatcgtg gtgtcacgct cgtcgtttgg tatggcttca ttcagctccg   2340
gttcccaacg atcaaggcga gttacatgat cccccatgtt gtgcaaaaaa gcggttagct   2400
ccttcggtcc tccgatcgtt gtcagaagta agttggccgc agtgttatca ctcatggtta   2460
tggcagcact gcataattct cttactgtca tgccatccgt aagatgcttt tctgtgactg   2520
gtgagtactc aaccaagtca ttctgagaat agtgtatgcg gcgaccgagt tgctcttgcc   2580
cggcgtcaat acgggataat accgcgccac atagcagaac tttaaaagtg ctcatcattg   2640
gaaaacgttc ttcggggcga aaactctcaa ggatcttacc gctgttgaga tccagttcga   2700
tgtaacccac tcgtgcaccc aactgatctt cagcatcttt tactttcacc agcgtttctg   2760
ggtgagcaaa aacaggaagg caaaatgccg caaaaaaggg aataagggcg acacggaaat   2820
```

```
gttgaatact catactcttc ctttttcaat attattgaag catttatcag ggttattgtc   2880

tcatgagcgg atacatattt gaatgtattt agaaaaataa acaaataggg gttccgcgca   2940

catttccccg aaaagtgcca c                                              2961
```

<210> SEQ ID NO 11
<211> LENGTH: 2335
<212> TYPE: DNA
<213> ORGANISM: Oryza sativa

<400> SEQUENCE: 11

```
acagattctt gctaccaaca acttcacaaa gtagtagtca accaaaacta tgctaaggaa     60

tcacctcact tccgcccatg accgtgagca cgactgttca aacagtttgt taatctctac    120

aaagaaggta cactttacct acacaacgcc actaacctga gttacccagc ccatgcaaaa    180

tagccacgtc ttgtgactta agggatttcg cgacaaggca tttcgaaagc ccacacaagg    240

acaccttatg aaaactggag gggtcccaca gaccaacaac aagttaggtc ccaaaccatg    300

ttgtgccagg aaaaatccaa ggggtcctcc ccaacaccac cccgacaaat ccacttgtcc    360

attggcatca agatttgcct gacctagcta attactcagc caggcatgtc acaattcacc    420

catgtggtca cacatgttag gttggagaaa ttctaaagga aaggaatcgg tccatatgag    480

caagaccgag aaaccatacc accagtactt ctaccgaaat acgagtttag taaactcatt    540

tgttttcaag gcacccgacc caggtgtgtc gggttttcca gggattttgt aaacccaagt    600

tttacccata gttgatcatt caaattttga ggagggtcat tggtatccgt acctgagggc    660

acgaatactg agacctagca ttgtagtcga ccaaggaggt taatgcagca attgtaggtg    720

gggcctgttg gttatattgc aaactgcggc caacatttca tgtgtaattt agagatgtgc    780

attttgagaa atgaaatact tagtttcaaa ttatgggctc aaataatgaa aggtgaccta    840

ccttgcttga tatcttgagc ttcttcctcg tattccgcgc actaggagat cttctggctc    900

cgaagctaca cgtggaacga gataactcaa caaaacgacc aaggaaaagc tcgtattagt    960

gagtactaag tgtgccactg aatagatctc gatttttgag gaattttaga agttgaacag   1020

agtcaatcga acagacagtt gaagagatat ggattttcta agattaattg attctctgta   1080

taaagaaaaa aagtattatt gaattaaatg gaaaaagaaa aaggaaaaag gggatggctt   1140

ctgctttttg ggctgaaggc ggcgtgtggc cagcgtgctg cgtgcggaca gcgagcgaac   1200

acacgacgga gcagctacga cgaacggggg accgagtgga ccggacgagg atgtggccta   1260

ggacgagtgc acaaggctag tggactcggt ccccgcgcgg tatcccgagt ggtccactgt   1320

ctgcaaacac gattcacata gagcgggcag acgcgggagc cgtcctaggt gcaccggaag   1380

caaatccgtc gcctgggtgg atttgagtga cacggcccac gtgtagcctc acagctctcc   1440

gtggtcagat gtgtaaaatt atcataatat gtgtttttca aatagttaaa taatatatat   1500

aggcaagtta tatgggtcaa taagcagtaa aaaggcttat gacatggtaa aattacttac   1560

accaatatgc cttactgtct gatatatttt acatgacaac aaagttacaa gtacgtcatt   1620

taaaaataca agttacttat caattgtagt gtatcaagta aatgacaaca aacctacaaa   1680

tttgctattt tgaaggaaca cttaaaaaaa tcaataggca agttatatag tcaataaact   1740

gcaagaaggc ttatgacatg gaaaaattac atacaccaat atgctttatt gtccggtata   1800

ttttacaaga caacaaagtt ataagtatgt catttaaaaa tacaagttac ttatcaattg   1860

tcaagtaaat gaaaacaaac ctacaaattt gttattttga aggaacacct aaattatcaa   1920
```

-continued

```
atatagcttg ctacgcaaaa tgacaacatg cttacaagtt attatcatct taaagttaga   1980

ctcatcttct caagcataag agctttatgg tgcaaaaaca aatataatga caaggcaaag   2040

atacatacat attaagagta tggacagaca tttctttaac aaactccatt tgtattactc   2100

caaaagcacc agaagtttgt catggctgag tcatgaaatg tatagttcaa tcttgcaaag   2160

ttgcctttcc ttttgtactg tgttttaaca ctacaagcca tatattgtct gtacgtgcaa   2220

caaactatat caccatgtat cccaagatgc ttttttattg ctatataaac tagcttggtc   2280

tgtctttgaa ctcacatcaa ttagcttaag tttccataag caagtacaaa tagct        2335
```

<210> SEQ ID NO 12
<211> LENGTH: 1474
<212> TYPE: DNA
<213> ORGANISM: Oryza sativa

<400> SEQUENCE: 12

```
tacagggttc cttgcgtgaa gaagggtggc ctgcggttca ccattaacgg tcacgactac     60

ttccagctag tactggtgac caacgtcgcg gcggcagggt caatcaagtc catggaggtt    120

atgggttcca acacagcgga ttggatgccg atggcacgta actggggcgc ccaatggcac    180

tcactggcct acctcaccgg tcaaggtcta tcctttaggg tcaccaacac agatgaccaa    240

acgctcgtct tcaccaacgt cgtgccacca ggatggaagt ttggccagac atttgcaagc    300

aagctgcagt tcaagtgaga ggagaagcct gaattgatac cggagcgttt cttttgggag    360

taacatctct ggttgcctag caaacatatg attgtatata agtttcgttg tgcgtttatt    420

ctttcggtgt gtaaaataac atacatgctt tcctgatatt ttcttgtata tatgtacaca    480

cacacgacaa atccttccat ttctattatt attgaacaat ttaattgcga gggcgagtac    540

ttgtctgttt accttttttt tttcagatgg cattttatag tttaaccttt catggaccgg    600

cagtagttct aaccatgaat gaaaagaaat catagtccac accacgcagg gacattgtgg    660

tcattttaga caagacgatt tgattaatgt cttgtatgat atggtcgaca gtgaggacta    720

acaaacatat ggcatatttt attaccggcg agttaaataa atttatgtca cagtaataaa    780

ctgcctaata aatgcacgcc agaaaatata atgataaaaa aaagaaaaga tacataagtc    840

cattgcttct actttttaa aaattaaatc caacattttc tattttttgg tataaacttg    900

gaagtactag ttggatatgc aaaatcatct aacctccata tatttcatca atttgtttac    960

tttacatatg ggagaggata gtatgtcaaa gaaaatgaca acaagcttac aagtttctta   1020

ttttaaaagt tccgctaact tatcaagcat agtgtgccac gcaaaactga caacaaacca   1080

acaaatttaa ggagcgccta acttatcatc tatgacatac cgcacaaaat gataacatac   1140

tagagaaact ttattgcaca aaaggaaatt tatccataag gcaaaggaac atcttaaggc   1200

tttggatata catttaccaa caagcattgt ttgtattacc cctaaagcgc aagacatgtc   1260

atccatgagt catagtgtgt atatctcaac attgcaaagc taccttttt ctattatact    1320

tttcgcatta taggctagat attatctata catgtcaaca aactctatcc ctacgtcata   1380

tctgaagatt cttttcttca ctatataagt tggcttccct gtcattgaac tcacatcaac   1440

cagcccaagt ttccaataac atcctcaaat agct                               1474
```

<210> SEQ ID NO 13
<211> LENGTH: 931
<212> TYPE: DNA
<213> ORGANISM: Oryza sativa

<400> SEQUENCE: 13

```
gatcttttaa ccgtgctacg ctgggttaat tagcgatggt gcaggtcacg tacccaaatt     60

tcttcactgt tggatcaact agagtagtta aacgagggca tgtgatgaag gctagctatt    120

tgaaattttc caattatccc tgcataagtc aggctacaat agcacctgga ctacatgcag    180

ggattacaaa ataggtggta accacattta ccgcgttaac cctatcaaat tcaaataaat    240

tttaaaagta atttgatttt tttaataaat tttgtatggt ttctcaagct ttattttggt    300

taccgtgctt actgcggagg caatgggaaa ccctcactag aagttgcacc tgttcttgtc    360

tgtgcaccat atcatgttga atcatgtgcg ttgtgtcttt cggaagaacc gatttactac    420

atgactcatc aattccactt tacgtatcaa aaggtttgtt atgggggcaa tgcttttgtg    480

aaattaaatt tttattttgc gtcacgttgt atctagttaa acactaccta cctaccatta    540

caaaacctca ttccacaaaa cgatgcatct agataaaaaa tatgacatgt aaagtgagta    600

atgactcatg tttattatca aaaatcgata acaatcaaat gatataggta gtaaagtacc    660

tttgaaatgg catgtccaag tatgtgtagc tccacctagc acaatatccc aagtgatcat    720

cataaaaggc atacaaatac aagcagccga tgatgcacac aagaaacaac acaaattgca    780

caaaaccaaa agcaaccgat gccttgagca tagagatcat gctattccca ctataaatac    840

aaatgcacca tatcaagatg ctcctcaccc ttactgaaaa atcacaaaca tcaaaacgtt    900

ataagagttc tctagcatcc atcacatagc c                                   931
```

<210> SEQ ID NO 14
<211> LENGTH: 824
<212> TYPE: DNA
<213> ORGANISM: Oryza sativa

<400> SEQUENCE: 14

```
actggataat tataatatca gttaaaattg aaaataatgc aacttcatac ttgcatggtg     60

tcagtagtgc ctgcctaaga aatgtgtctt gtcataatat gattacatga aatatgttta    120

cttcctcgtt tctctttatt tgtaagataa agaactagat atgtggaaag taggatagca    180

aagagtatgg ccaaactcta atctttgctt tattttttgg gatggaccca aaatttgttt    240

ctcctttact tctttccctt tacaacaatg ttctttactt ccaattctta ttaacaaaac    300

tccaaataca tgccaaactg catatgtatg tatgctatta aggcacattt acaaagctcc    360

aagtttacct actcaatcat tcacatatgg cgatgactca aactcttaat tgttatctgg    420

taagctgtga cttgtgtaac acattctaca agtcccatac gaattctgtt cacaaaagtt    480

tctttgtcca gctcataatt tacaaaactg caaaatgcca aagcaatctg gcacaacctt    540

atcatcatat tttctttcca cgcattaaag cactggcaga attatctttg tgtagatatt    600

ccaaaagtat tggttgaata aatgtccaaa taaattccat gcctcatgat ttccagctta    660

tgtggcctcc actaggtggt tttgcaaagg ccaaactctt tcctggctta cacagctacc    720

agcatgtata aataggcccc taggcaacca ttattccatc atcctcaaca atattgtcta    780

caccatctgg aatcttgttt aacactagta ttgtagaatc agca                     824
```

<210> SEQ ID NO 15
<211> LENGTH: 1672
<212> TYPE: DNA
<213> ORGANISM: Artificial
<220> FEATURE:
<223> OTHER INFORMATION: GluA2 having Cfr9I site

<400> SEQUENCE: 15

```
gttcattagt cctacaacaa catggcatcc ataaatcgcc ccatagtttt cttcacagtt     60

tgcttgttcc tcttgtgcga tggctcccta gcccagcagc tattaggcca gagcactagt    120

caatggcaga gttctcgtcg tggaagtccg agaggatgta gatttgatag gttgcaagca    180

tttgagccaa ttcggagtgt gaggtctcaa gctggcacaa ctgagttctt cgatgtctct    240

aatgagttgt ttcaatgtac cggagtatct gttgtccgcc gagttattga acctagaggc    300

ctactactac cccattacac taatggtgca tctctagtat atatcatcca agggagaggt    360

ataacagggc cgactttccc aggctgtcct gagacctacc agcagcagtt ccaacaatca    420

gggcaagccc aattgaccga aagtcaaagc caaagccata agttcaagga tgaacatcaa    480

aagattcacc gtttcagaca aggagatgtt atcgcgttgc ctgctggtgt agctcattgg    540

tgctacaatg atggtgaagt gccggttgtt gccatatatg tcactgatat caacaacggt    600

gctaatcaac ttgaccctcg acagagggat ttcttgttag ctggaaataa gagaaaccct    660

caagcataca ggcgtgaagt tgaggagtgg tcacaaaaca tatttagtgg ctttagcact    720

gaactgctta gcgaggcttt tggcataagc aaccaagttg caaggcagct ccagtgtcaa    780

aatgaccaaa gaggagaaat tgtccgcgtt gaacgcgggc tcagtttgct gcaaccatat    840

gcatcacccg ggcctaacgg tttggatgag accttttgca ccatgagggt aaggcaaaac    900

atcgataatc ctaaccgtgc tgatacatac aacccaagag ctggaagggt tacaaatctc    960

aacagccaga atttccccat tcttaatctt gtacagatga gcgccgttaa agtaaatcta   1020

taccagaatg cactcctttc accgttctgg aacatcaacg ctcacagcat cgtgtatatt   1080

actcaaggcc gagcccaggt tcaagttgtc aacaacaatg gaaagacggt gttcaacgga   1140

gagcttcgtc gtggacagct acttattgta ccacaacact atgtagttgt aaagaaggca   1200

caaagagaag gatgtgctta cattgcattc aagacaaacc ctaactctat ggtaagccac   1260

attgcaggaa agagttccat cttccgtgct ctcccaactg atgttctagc aaatgcatat   1320

cgcatctcaa gagaagaggc tcagaggctc aagcataaca gaggagatga gttcggtgca   1380

ttcactcccc tccaatacaa gagctaccaa gacgtttata atgtggcgga atcctcttaa   1440

gttggcaatg cggataaaga ataactaaat aaataaataa ataaattgca agcaattgcg   1500

ttgctgctat gtactgtaaa agtttcttat aatatcagtt ctgaatgcta aggacatccc   1560

tcaagatggt ctttctattt ttgtgttccc gttccaatgt actgttcgta tcctcttgga   1620

gattcatcaa tatgagaaaa cagagaatgg acaaccctcc cttatcttat gg           1672
```

```
<210> SEQ ID NO 16
<211> LENGTH: 1672
<212> TYPE: DNA
<213> ORGANISM: Artificial
<220> FEATURE:
<223> OTHER INFORMATION: GluB1 having Cfr9I site

<400> SEQUENCE: 16
```

```
gttcattagt cctacaacaa catggcatcc ataaatcgcc ccatagtttt cttcacagtt     60

tgcttgttcc tcttgtgcga tggctcccta gcccagcagc tattaggcca gagcactagt    120

caatggcaga gttctcgtcg tggaagtccg agaggatgta gatttgatag gttgcaagca    180

tttgagccaa ttcggagtgt gaggtctcaa gctggcacaa ctgagttctt cgatgtctct    240

aatgagttgt ttcaatgtac cggagtatct gttgtccgcc gagttattga acctagaggc    300

ctactactac cccattacac taatggtgca tctctagtat atatcatcca agggagaggt    360

ataacagggc cgactttccc aggctgtcct gagacctacc agcagcagtt ccaacaatca    420
```

```
gggcaagccc aattgaccga aagtcaaagc caaagccata agttcaagga tgaacatcaa    480

aagattcacc gtttcagaca aggagatgtt atcgcgttgc ctgctggtgt agctcattgg    540

tgctacaatg atggtgaagt gccggttgtt gccatatatg tcactgatat caacaacggt    600

gctaatcaac ttgaccctcg acagagggat ttcttgttag ctggaaataa gagaaaccct    660

caagcataca ggcgtgaagt tgaggagtgg tcacaaaaca tatttagtgg ctttagcact    720

gaactgctta gcgaggcttt tggcataagc aaccaagttg caaggcagct ccagtgtcaa    780

aatgaccaaa gaggagaaat tgtccgcgtt gaacgcgggc tcagtttgct gcaaccatat    840

gcatcacccg ggcctaacgg tttggatgag accttttgca ccatgagggt aaggcaaaac    900

atcgataatc ctaaccgtgc tgatacatac aacccaagag ctggaagggt tacaaatctc    960

aacagccaga atttccccat tcttaatctt gtacagatga gcgccgttaa agtaaatcta   1020

taccagaatg cactcctttc accgttctgg aacatcaacg ctcacagcat cgtgtatatt   1080

actcaaggcc gagcccaggt tcaagttgtc aacaacaatg gaaagacggt gttcaacgga   1140

gagcttcgtc gtggacagct acttattgta ccacaacact atgtagttgt aaagaaggca   1200

caaagagaag gatgtgctta cattgcattc aagacaaacc ctaactctat ggtaagccac   1260

attgcaggaa agagttccat cttccgtgct ctcccaactg atgttctagc aaatgcatat   1320

cgcatctcaa gagaagaggc tcagaggctc aagcataaca gaggagatga gttcggtgca   1380

ttcactcccc tccaatacaa gagctaccaa gacgtttata atgtggcgga atcctcttaa   1440

gttggcaatg cggataaaga ataactaaat aaataaataa ataaattgca agcaattgcg   1500

ttgctgctat gtactgtaaa agtttcttat aatatcagtt ctgaatgcta aggacatccc   1560

tcaagatggt ctttctattt ttgtgttccc gttccaatgt actgttcgta tcctcttgga   1620

gattcatcaa tatgagaaaa cagagaatgg acaaccctcc cttatcttat gg           1672
```

```
<210> SEQ ID NO 17
<211> LENGTH: 1529
<212> TYPE: DNA
<213> ORGANISM: Artificial
<220> FEATURE:
<223> OTHER INFORMATION: GluC having Cfr9I site

<400> SEQUENCE: 17

ggatccatgg cttccatgtc taccattctt ccattgtgcc ttggcctcct tctcttcttc     60

caagtgtcca tggcacaatt ttcatttggg ggaagcccac ttcagagccc acgtggattt    120

aggggagacc aagatagtcg tcatcaatgt cgttttgagc acctcaccgc ccttgaggca    180

acacaccagc agagatctga agctggattc actgagtact acaacattga ggcaagaaat    240

gagttccgtt gtgccggagt gagcgtgagg cgcttagtcg tcgagagcaa gggcttagtt    300

ttaccaatgt atgctaatgc tcacaagctt gtctacatcg tccaaggtcg gggagtgttt    360

gggatggcac tgcctggttg tccagagacg ttccagtcag ttaggtctcc ctttgagcaa    420

gaggtggcaa cagctggtga ggctcaatca tcaatccaaa aaatgagaga cgagcaccag    480

caacttcacc aattccacca aggtgatgta atcgcagtgc cagctggagt agcccactgg    540

ctatataaca atggtgattc tcctgtggtt gctttcactg tcatcgacac cagcaacaat    600

gccaaccagc tcgatcctaa aagaagggag tttttcttgg ctggaaagcc tagaagtagc    660

tggcagcagc aatcgtactc ataccagaca gaacaactga gcagaaatca gaacatcttt    720

gctgggttca gcccagattt actttctgaa gccctgagtg tgagcaagca aactgtgttg    780
```

```
aggctccaag gcctgagtga cccaagaggt gccatcatta gagttgaaaa tgggctccag    840

gcactgcccg ggaatggact agatgaaatt atgtgtgcat ttaagttgag gaagaacata    900

gacaacccac aatccagtga catatttaac ccccatggtg gaaggatcac aagggccaat    960

agccagaatt tcccaatact caatatcatc cagatgagtg ccaccagaat cgttctccaa   1020

aataatgcct tgcttactcc tcattggacg gtaaacgcac acacggtgat gtacgtgacc   1080

gctggccaag ggcacatcca ggtggtggat caccgtggta ggagtgtctt tgatggtgag   1140

cttcaccaac agcagatctt gttgatccca cagaactttg cagtggtggt gaaggctcga   1200

cgtgaaggat ttgcatgggt atccttcaag accaatcaca atgctgtcga cagtcagatc   1260

gcagggaagg cctccattct tcgtgctcta cccgttgacg tggtcgccaa tgcttatagg   1320

ctttcaaggg aggactctag gcatgtaaag ttcaaccgcg gcgatgagat ggctgtcttt   1380

gctccgaggc gtgggccgca acagtatgct gagtggcaga tcaacgagaa gtaaactaaa   1440

tgtgtaacga tcttactgta atgaataatg tgaagaagat tgcctacacc tctttttcca   1500

taaaaataag aattactaag aacgagctc                                     1529
```

<210> SEQ ID NO 18
<211> LENGTH: 627
<212> TYPE: DNA
<213> ORGANISM: Oryza sativa

<400> SEQUENCE: 18

```
taattgagaa ctagtatcgg cgtagagtaa aataaaacac cacaagtatg acacttggtg     60

gtgattctgt tcgatatcag tactaaataa aggttacaaa cttcttaatt ttcctacttc    120

atgccatgga tattccatta tggactatag tggacagggc cggtctatga ttttgagggc    180

cctaggaact catcgcgatg ggcctcaagc tatatataaa atttattgat atatatagac    240

gctaatttta cttgcaaaat gaaaacaaat acatctatat attaaattta acattcctgg    300

taattatcaa gaaataaaat cgaccaaaat aacaatatat ttgtaacttg gaactaatat    360

aattatttat taacttaatg aagaatagaa ccccgtcata tccattgctt cctatgaaaa    420

gatacttctt cgggtatttc ttgatgcaaa atcataaaga acggtattaa gatcaatagt    480

gtccaagata tccttctcga ttgagcacat agccaagcca tttaacctta tttgcgacag    540

ttgatctcaa atagtttttc aacaacttca attttgataa acttatttca gctgaagcta    600

ccatcatagg taaagttaag agaattc                                        627
```

<210> SEQ ID NO 19
<211> LENGTH: 654
<212> TYPE: DNA
<213> ORGANISM: Oryza sativa

<400> SEQUENCE: 19

```
tgtactaatg aaatggtata ggtgtatcaa aaaaaaataa aatgccacaa gtatgtgaaa     60

ctttgtggcg gttctgttct aagtttatga agcactaata aaatgctaca actgttttat    120

tcatgcaatt tttgctacag gacatcgtga cttcgcgatt ttagctgtag gacactacgc    180

gaagtgactt ttgggagaag acactacgta aagatggaaa ttagctcgtg gacaacgcgc    240

ctattcgaat attcatcttt aattgaattg gtgagagaaa ccacatgaaa atattaaaat    300

acccctggtc ccaaatgcca agtcttgcat ctctctctgt ctatctctct cacacagaag    360

cgtctcaact agcatgttgt actaccggga ggtctgccgc ctgcacaagg atgggaggag    420

gcagagcacc ttgaccacct ggtccatgaa actcaaaatc acattacctg catgggctgc    480
```

cgctactaag caatcaactg tggactcata aacacttgaa ccaaatgcat gatccgcagt 540
ccccaattcg acaaccccaa agcgacattc ccaacactga tgagaaacga tttagaagac 600
gacccatccg acgacgaaga cactatcgcc gccctaccag ggagaaagct cgat 654

<210> SEQ ID NO 20
<211> LENGTH: 309
<212> TYPE: DNA
<213> ORGANISM: Oryza sativa

<400> SEQUENCE: 20
tagtgtgtac catcatatat atatagttgg ataaagtgtc acacatcatc gtgtgtgtca 60
tgtaataaaa tttggtttag tctttagctg ttcgtatgaa taaatgaaaa ttataacatg 120
tccaattgtt gcaaacaggc attgtgcgta tccagtggct gcattaattt tcggttttac 180
tgtacataca aatttcatca tattattctt ttttgttttc atactaagaa agagaagcaa 240
atcaatataa tatattaatc tgatcttgta gaaatgaaaa gatgagatac tcaaagttat 300
ggttaattg 309

<210> SEQ ID NO 21
<211> LENGTH: 279
<212> TYPE: DNA
<213> ORGANISM: Oryza sativa

<400> SEQUENCE: 21
tgatcaaacg ttggttacat gtactctagt aataaggtgt tgcatactat cgtgtgcaaa 60
cactagaaat aagaaccatt gaataaaata tcaatcattt tcagacttgc aaatattggg 120
tatttggatt tctgtcccat gtccctcttg aaagccatgc tgtacatgtt ggagttcccc 180
cttggaccca acctactcca tgctcccatg ttgatcttaa attccctgtt cccccagagc 240
atgtaaattt tcttatgcta atcagagcaa gctcgatgt 279

<210> SEQ ID NO 22
<211> LENGTH: 10327
<212> TYPE: DNA
<213> ORGANISM: Artificial
<220> FEATURE:
<223> OTHER INFORMATION: destination binary vector

<400> SEQUENCE: 22
gagcggataa caatttcaca caggaaacag ctatgaccat gattacgcca agctatcaac 60
tttgtataga aaagttgaac gagaaacgta aaatgatata aatatcaata tattaaatta 120
gattttgcat aaaaaacaga ctacataata ctgtaaaaca caacatatcc agtcactatg 180
gtcgacctgc agactggctg tgtataaggg agcctgacat ttatattccc cagaacatca 240
ggttaatggc gtttttgatg tcattttcgc ggtggctgag atcagccact tcttccccga 300
taacggagac cggcacactg gccatatcgg tggtcatcat gcgccagctt tcatccccga 360
tatgcaccac cgggtaaagt tcacgggga ctttatctga cagcagacgt gcactggcca 420
gggggatcac catccgtcgc ccgggcgtgt caataatatc actctgtaca tccacaaaca 480
gacgataacg gctctctctt ttataggtgt aaaccttaaa ctgcatttca ccagcccctg 540
ttctcgtcgg caaaagagcc gttcatttca ataaaccggg cgacctcagc catcccttcc 600
tgattttccg ctttccagcg ttcggcacgc agacgacggg cttcattctg catggttgtg 660
cttaccgaac cggagatatt gacatcatat atgccttgag caactgatag ctgtcgctgt 720

```
caactgtcac tgtaatacgc tgcttcatag catacctctt tttgacatac ttcgggtata    780
catatcagta tatattctta taccgcaaaa atcagcgcgc aaatacgcat actgttatct    840
ggcttttagt aagccggatc ctctagatta cgccccgccc tgccactcat cgcagtactg    900
ttgtaattca ttaagcattc tgccgacatg gaagccatca caaacggcat gatgaacctg    960
aatcgccagc ggcatcagca ccttgtcgcc ttgcgtataa tatttgccca tggtgaaaac   1020
gggggcgaag aagttgtcca tattggccac gtttaaatca aaactggtga aactcaccca   1080
gggattggct gagacgaaaa acatattctc aataaaccct ttagggaaat aggccaggtt   1140
ttcaccgtaa cacgccacat cttgcgaata tatgtgtaga aactgccgga aatcgtcgtg   1200
gtattcactc cagagcgatg aaaacgtttc agtttgctca tggaaaacgg tgtaacaagg   1260
gtgaacacta tcccatatca ccagctcacc gtctttcatt gccatacgga attccggatg   1320
agcattcatc aggcgggcaa gaatgtgaat aaaggccgga taaaacttgt gcttattttt   1380
ctttacggtc tttaaaaagg ccgtaatatc cagctgaacg gtctggttat aggtacattg   1440
agcaactgac tgaaatgcct caaaatgttc tttacgatgc cattgggata tatcaacggt   1500
ggtatatcca gtgatttttt tctccatttt agcttcctta gctcctgaaa atctcgacgg   1560
atcctaactc aaaatccaca cattatacga gccggaagca taaagtgtaa agcctggggg   1620
tgcctaatgc ggccgccata gtgactggat atgttgtgtt ttacagtatt atgtagtctg   1680
tttttatgc aaaatctaat ttaatatatt gatatttata tcattttacg tttctcgttc    1740
aactttatta tacatagttg ataattcact ggccgtcgtt ttacaacgtc gtgactggga   1800
aaacgagctc aagcttagct tgagcttgga tcagattgtc gtttcccgcc ttcagtttaa   1860
actatcagtg tttgacagga tatattggcg ggtaaaccta agagaaaaga gcgtttatta   1920
gaataacgga tatttaaaag ggcgtgaaaa ggtttatccg ttcgtccatt tgtatgtgca   1980
tgccaaccac agggttcccc tcgggatcaa agtactttga tccaacccct ccgctgctat   2040
agtgcagtcg gcttctgacg ttcagtgcag ccgtcttctg aaaacgacat gtcgcacaag   2100
tcctaagtta cgcgacaggc tgccgccctg cccttttcct ggcgttttct tgtcgcgtgt   2160
tttagtcgca taaagtagaa tacttgcgac tagaaccgga gacattacgc catgaacaag   2220
agcgccgccg ctggcctgct gggctatgcc cgcgtcagca ccgacgacca ggacttgacc   2280
aaccaacggg ccgaactgca cgcggccggc tgcaccaagc tgttttccga gaagatcacc   2340
ggcaccaggc gcgaccgccc ggagctggcc aggatgcttg accacctacg ccctggcgac   2400
gttgtgacag tgaccaggct agaccgcctg gcccgcagca cccgcgacct actggacatt   2460
gccgagcgca tccaggaggc cggcgcgggc ctgcgtagcc tggcagagcc gtgggccgac   2520
accaccacgc cggccggccg catggtgttg accgtgttcg ccggcattgc cgagttcgag   2580
cgttccctaa tcatcgaccg cacccggagc gggcgcgagg ccgccaaggc ccgaggcgtg   2640
aagtttggcc cccgccctac cctcaccccg gcacagatcg cgcacgcccg cgagctgatc   2700
gaccaggaag gccgcaccgt gaaagaggcg gctgcactgc ttggcgtgca tcgctcgacc   2760
ctgtaccgcg cacttgagcg cagcgaggaa gtgacgccca ccgaggccag gcggcgcggt   2820
gccttccgtg aggacgcatt gaccgaggcc gacgccctgg cggccgccga gaatgaacgc   2880
caagaggaac aagcatgaaa ccgcaccagg acggccagga cgaaccgttt ttcattaccg   2940
aagagatcga ggcggagatg atcgcggccg ggtacgtgtt cgagccgccc gcgcacgtct   3000
caaccgtgcg gctgcatgaa atcctggccg gtttgtctga tgccaagctg gcggcctggc   3060
cggccagctt ggccgctgaa gaaaccgagc gccgccgtct aaaaaggtga tgtgtatttg   3120
```

```
agtaaaacag cttgcgtcat gcggtcgctg cgtatatgat gcgatgagta aataaacaaa   3180
tacgcaaggg gaacgcatga aggttatcgc tgtacttaac cagaaaggcg ggtcaggcaa   3240
gacgaccatc gcaacccatc tagcccgcgc cctgcaactc gccggggccg atgttctgtt   3300
agtcgattcc gatccccagg gcagtgcccg cgattgggcg gccgtgcggg aagatcaacc   3360
gctaaccgtt gtcggcatcg accgcccgac gattgaccgc gacgtgaagg ccatcggccg   3420
gcgcgacttc gtagtgatcg acggagcgcc ccaggcggcg gacttggctg tgtccgcgat   3480
caaggcagcc gacttcgtgc tgattccggt gcagccaagc ccttacgaca tatgggccac   3540
cgccgacctg gtggagctgg ttaagcagcg cattgaggtc acggatggaa ggctacaagc   3600
ggcctttgtc gtgtcgcggg cgatcaaagg cacgcgcatc ggcggtgagg ttgccgaggc   3660
gctggccggg tacgagctgc ccattcttga gtcccgtatc acgcagcgcg tgagctaccc   3720
aggcactgcc gccgccggca caaccgttct tgaatcagaa cccgagggcg acgctgcccg   3780
cgaggtccag gcgctggccg ctgaaattaa atcaaaactc atttgagtta atgaggtaaa   3840
gagaaaatga gcaaaagcac aaacacgcta agtgccggcc gtccgagcgc acgcagcagc   3900
aaggctgcaa cgttggccag cctggcagac acgccagcca tgaagcgggt caactttcag   3960
ttgccggcgg aggatcacac caagctgaag atgtacgcgg tacgccaagg caagaccatt   4020
accgagctgc tatctgaata catcgcgcag ctaccagagt aaatgagcaa atgaataaat   4080
gagtagatga attttagcgg ctaaaggagg cggcatggaa aatcaagaac aaccaggcac   4140
cgacgccgtg gaatgcccca tgtgtggagg aacgggcggt tggccaggcg taagcggctg   4200
ggttgtctgc cggccctgca atggcactgg aacccccaag cccgaggaat cggcgtgacg   4260
gtcgcaaacc atccggcccg gtacaaatcg gcgcggcgct gggtgatgac ctggtggaga   4320
agttgaaggc cgcgcaggcc gcccagcggc aacgcatcga ggcagaagca cgccccggtg   4380
aatcgtggca agcggccgct gatcgaatcc gcaaagaatc ccggcaaccg ccggcagccg   4440
gtgcgccgtc gattaggaag ccgcccaagg gcgacgagca accagatttt ttcgttccga   4500
tgctctatga cgtgggcacc cgcgatagtc gcagcatcat ggacgtggcc gttttccgtc   4560
tgtcgaagcg tgaccgacga gctggcgagg tgatccgcta cgagcttcca gacgggcacg   4620
tagaggtttc cgcagggccg gccggcatgg ccagtgtgtg ggattacgac ctggtactga   4680
tggcggtttc ccatctaacc gaatccatga accgataccg ggaagggaag ggagacaagc   4740
ccggccgcgt gttccgtcca cacgttgcgg acgtactcaa gttctgccgg cgagccgatg   4800
gcggaaagca gaaagacgac ctggtagaaa cctgcattcg gttaaacacc acgcacgttg   4860
ccatgcagcg tacgaagaag gccaagaacg gccgcctggt gacggtatcc gagggtgaag   4920
ccttgattag ccgctacaag atcgtaaaga gcgaaaccgg gcggccggag tacatcgaga   4980
tcgagctagc tgattggatg taccgcgaga tcacagaagg caagaacccg gacgtgctga   5040
cggttcaccc cgattacttt ttgatcgatc ccggcatcgg ccgttttctc taccgcctgg   5100
cacgccgcgc cgcaggcaag gcagaagcca gatggttgtt caagacgatc tacgaacgca   5160
gtggcagcgc cggagagttc aagaagttct gtttcaccgt gcgcaagctg atcgggtcaa   5220
atgacctgcc ggagtacgat ttgaaggagg aggcggggca ggctggcccg atcctagtca   5280
tgcgctaccg caacctgatc gagggcgaag catccgccgg ttcctaatgt acggagcaga   5340
tgctagggca aattgcccta gcaggggaaa aaggtcgaaa aggtctcttt cctgtggata   5400
gcacgtacat tgggaaccca aagccgtaca ttgggaaccg gaacccgtac attgggaacc   5460
```

```
caaagccgta cattgggaac cggtcacaca tgtaagtgac tgatataaaa gagaaaaaag   5520

gcgatttttc cgcctaaaac tctttaaaac ttattaaaac tcttaaaacc cgcctggcct   5580

gtgcataact gtctggccag cgcacagccg aagagctgca aaaagcgcct acccttcggt   5640

cgctgcgctc cctacgcccc gccgcttcgc gtcggcctat cgcggccgct ggccgctcaa   5700

aaatggctgg cctacggcca ggcaatctac cagggcgcgg acaagccgcg ccgtcgccac   5760

tcgaccgccg gcgcccacat caaggcaccc tgcctcgcgc gtttcggtga tgacggtgaa   5820

aacctctgac acatgcagct cccggagacg gtcacagctt gtctgtaagc ggatgccggg   5880

agcagacaag cccgtcaggg cgcgtcagcg ggtgttggcg ggtgtcgggg cgcagccatg   5940

acccagtcac gtagcgatag cggagtgtat actggcttaa ctatgcggca tcagagcaga   6000

ttgtactgag agtgcaccat atgcggtgtg aaataccgca cagatgcgta aggagaaaat   6060

accgcatcag gcgctcttcc gcttcctcgc tcactgactc gctgcgctcg gtcgttcggc   6120

tgcggcgagc ggtatcagct cactcaaagg cggtaatacg gttatccaca gaatcagggg   6180

ataacgcagg aaagaacatg tgagcaaaag gccagcaaaa ggccaggaac cgtaaaaagg   6240

ccgcgttgct ggcgtttttc cataggctcc gcccccctga cgagcatcac aaaaatcgac   6300

gctcaagtca gaggtggcga aacccgacag gactataaag ataccaggcg tttccccctg   6360

gaagctccct cgtgcgctct cctgttccga ccctgccgct taccggatac ctgtccgcct   6420

ttctcccttc gggaagcgtg gcgctttctc atagctcacg ctgtaggtat ctcagttcgg   6480

tgtaggtcgt tcgctccaag ctgggctgtg tgcacgaacc ccccgttcag cccgaccgct   6540

gcgccttatc cggtaactat cgtcttgagt ccaacccggt aagacacgac ttatcgccac   6600

tggcagcagc cactggtaac aggattagca gagcgaggta tgtaggcggt gctacagagt   6660

tcttgaagtg gtggcctaac tacggctaca ctagaaggac agtatttggt atctgcgctc   6720

tgctgaagcc agttaccttc ggaaaaagag ttggtagctc ttgatccggc aaacaaacca   6780

ccgctggtag cggtggtttt tttgtttgca agcagcagat tacgcgcaga aaaaaaggat   6840

ctcaagaaga tcctttgatc ttttctacgg ggtctgacgc tcagtggaac gaaaactcac   6900

gttaagggat tttggtcatg catgatatat ctcccaattt gtgtagggct tattatgcac   6960

gcttaaaaat aataaaagca gacttgacct gatagtttgg ctgtgagcaa ttatgtgctt   7020

agtgcatcta atcgcttgag ttaacgccgg cgaagcggcg tcggcttgaa cgaatttcta   7080

gctagacatt atttgccgac taccttggtg atctcgcctt tcacgtagtg gacaaattct   7140

tccaactgat ctgcgcgcga ggccaagcga tcttcttctt gtccaagata agcctgtcta   7200

gcttcaagta tgacgggctg atactgggcc ggcaggcgct ccattgccca gtcggcagcg   7260

acatccttcg gcgcgatttt gccggttact gcgctgtacc aaatgcggga caacgtaagc   7320

actacatttc gctcatcgcc agcccagtcg ggcggcgagt tccatagcgt taaggtttca   7380

tttagcgcct caaatagatc ctgttcagga accggatcaa agagttcctc cgccgctgga   7440

cctaccaagg caacgctatg ttctcttgct tttgtcagca agatagccag atcaatgtcg   7500

atcgtggctg gctcgaagat acctgcaaga atgtcattgc gctgccattc tccaaattgc   7560

agttcgcgct tagctggata acgccacgga atgatgtcgt cgtgcacaac aatggtgact   7620

tctacagcgc ggagaatctc gctctctcca ggggaagccg aagtttccaa aaggtcgttg   7680

atcaaagctc gccgcgttgt ttcatcaagc cttacggtca ccgtaaccag caaatcaata   7740

tcactgtgtg gcttcaggcc gccatccact gcggagccgt acaaatgtac ggccagcaac   7800

gtcggttcga gatggcgctc gatgacgcca actacctctg atagttgagt cgatacttcg   7860
```

```
gcgatcaccg cttcccccat gatgtttaac tttgttttag ggcgactgcc ctgctgcgta   7920
acatcgttgc tgctccataa catcaaacat cgacccacgg cgtaacgcgc ttgctgcttg   7980
gatgcccgag gcatagactg taccccaaaa aaacatgtca taacaagaag ccatgaaaac   8040
cgccactgcg ccgttaccac cgctgcgttc ggtcaaggtt ctggaccagt tgcgtgacgg   8100
cagttacgct acttgcatta cagcttacga accgaacgag gcttatgtcc actgggttcg   8160
tgcccgaatt gatcacaggc agcaacgctc tgtcatcgtt acaatcaaca tgctaccctc   8220
cgcgagatca tccgtgtttc aaacccggca gcttagttgc cgttcttccg aatagcatcg   8280
gtaacatgag caaagtctgc cgccttacaa cggctctccc gctgacgccg tcccggactg   8340
atgggctgcc tgtatcgagt ggtgattttg tgccgagctg ccggtcgggg agctgttggc   8400
tggctggtgg caggatatat tgtggtgtaa acaaattgac gcttagacaa cttaataaca   8460
cattgcggac gtttttaatg tactgaatta acgccgaatt gaattatcag cttgcatgcc   8520
ggtcgatcta gtaacataga tgacaccgcg cgcgataatt tatcctagtt tgcgcgctat   8580
attttgtttt ctatcgcgta ttaaatgtat aattgcggga ctctaatcat aaaaacccat   8640
ctcataaata acgtcatgca ttacatgtta attattacat gcttaacgta attcaacaga   8700
aattatatga taatcatcgc aagaccggca acaggattca atcttaagaa actttattgc   8760
caaatgtttg aacgatctgc ttgactctag ggaattaatt cctgaatcac tgcgaccggc   8820
cctcccgcga cccagccgag cgagcttagc gaactgtgga cgagaactgt gccaccaagc   8880
gtaaggccgt tctctcgcat ttgccttgct aggctcgcgc gagttgctgg ctgaggcgtt   8940
ctcgaaatca gctcttgttc ggtcggcatc tactctattc ctttgccctc ggacgagtgc   9000
tggggcgtcg gtttccacta tcggcgagta cttctacaca gccatcggtc cagacggccg   9060
cgcttctgcg ggcgatttgt gtacgcccga cagtcccggc tccggatcgg acgattgcgt   9120
cgcatcgacc ctgcgcccaa gctgcatcat cgaaattgcc gtcaaccaag ctctgataga   9180
gttggtcaag accaatgcgg agcatatacg cccggagcct tggcgatcct gcaagctccg   9240
gatgcctccg ctcgaagtag cgcgtctgct gctccataca agccaaccac ggcctccaga   9300
agaagatgtt ggcgacctcg tattgggaat ccccgaacat cgcctcgctc cagtcaatga   9360
ccgctgttat gcggccattg tccgtcagga cattgttgga gccgaatccg cgtgcacgag   9420
tgccggactt cggggcagtc ctcgcccaaa gcatcagctc atcgagagcc tgcgcgacgg   9480
acgcactgac ggtgtcgtcc atcacagttt gccagtgata cacatgggga tcagcaatcg   9540
cgcatatgaa atcacgccat gtagtgtatt gaccgattcc ttgcggtccg aatgggccga   9600
acccgctcgt ctggctaaga tcggccgcag cgatagcatc catagcctcc gcgaccggct   9660
gaagaacagc gggcagttcg gtttcaggca ggtcttgcaa cgtgacaccc tgtgcacggc   9720
gggagatgca ataggtcagg ctctcgctga actccccaat gtcaagcact tccggaatcg   9780
ggagcgcggc cgatgcaaag tgccgataaa cataacgatc tttgtagaaa ccatcggcgc   9840
agctatttac ccgcaggaca tatccacgcc ctcctacatc gaagctgaaa gcacgagatt   9900
cttcgccctc cgagagctgc atcaggtcgg agacgctgtc gaacttttcg atcagaaact   9960
tctcgacaga cgtcgcggtg agttcaggct ttttcatagg ggggattcga gttgagagtg  10020
aatatgagac tctaattgga taccgagggg aatttatgga acgtcagtgg agcatttttg  10080
```

-continued

```
acaagaaata tttgctagct gatagtgacc ttaggcgact tttgaacgcg caataatggt  10140

ttctgacgta tgtgcttagc tcattaaact ccagaaaccc gcggctcagt ggctccttca  10200

acgttgcggt tctgtcagtt ccaaacgtaa aacggcttgt cccgcgtcat cggcggggtc  10260

ataacgtgac tcccttaatt ctcatgtatg ataattcgag ggtacccggg gatcctctag  10320

agggccc                                                            10327
```